United States Patent
Yin et al.

(10) Patent No.: US 10,457,690 B2
(45) Date of Patent: Oct. 29, 2019

(54) PROCESS FOR PREPARING SUBSTITUTED TETRACYCLIC HETEROCYCLE COMPOUNDS

(71) Applicant: MERCK SHARP & DOHME CORP., Rahway, NJ (US)

(72) Inventors: Jingjun Yin, Green Brook, NJ (US); Tetsuji Itoh, Somerset, NJ (US); Jianguo Yin, Plainsboro, NJ (US); Bangping Xiang, Bridgewater, NJ (US); Kevin R. Campos, Berkeley Heights, NJ (US); Alexei Kalinin, Morganville, NJ (US); Zhuqing Liu, Edison, NJ (US); Melodie Deniz Christensen, New York, NY (US); Kevin M. Belyk, Metuchen, NJ (US); Richard J. Varsolona, Scotch Plains, NJ (US); Andrew Brunskill, Watchung, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/578,777

(22) PCT Filed: Jun. 3, 2016

(86) PCT No.: PCT/US2016/035717
§ 371 (c)(1),
(2) Date: Dec. 1, 2017

(87) PCT Pub. No.: WO2016/196932
PCT Pub. Date: Dec. 8, 2016

(65) Prior Publication Data
US 2018/0179223 A1  Jun. 28, 2018

Related U.S. Application Data

(60) Provisional application No. 62/171,039, filed on Jun. 4, 2015.

(51) Int. Cl.
*C07D 498/04* (2006.01)
*C07D 403/04* (2006.01)
*C07F 5/02* (2006.01)
*B01J 31/04* (2006.01)

(52) U.S. Cl.
CPC .......... *C07D 498/04* (2013.01); *B01J 31/04* (2013.01); *C07D 403/04* (2013.01); *C07F 5/025* (2013.01)

(58) Field of Classification Search
CPC .................................................. C07D 498/04
USPC ............................................................ 544/95
See application file for complete search history.

(56) References Cited

U.S. PATENT DOCUMENTS

| 4,198,524 A | 4/1980 | Tashiro et al. |
| 2012/0083483 A1 | 4/2012 | Coburn et al. |
| 2014/0213571 A1 | 7/2014 | Liverton et al. |

FOREIGN PATENT DOCUMENTS

| WO | WO2012041014 A1 | 4/2012 |
| WO | WO2014110705 A1 | 7/2014 |
| WO | WO2014110706 A1 | 7/2014 |
| WO | 2015065821 A1 | 5/2015 |
| WO | 2016004899 A1 | 1/2016 |

OTHER PUBLICATIONS

International Search Report and Written Opinion for PCT/US2016/035717, dated Sep. 2, 2016, 9 pages.
Kabalka, George W., et al, "Pd-Catalyzed Cross-Coupling of Baylis-Hillman Acetate Adducts with Bis (pinacolato)diboron: An Efficient Route to Functionalized Allyl Borates", J. Org. Chem., 2004, pp. 5807-5809, vol. 69.
Tan, et al, "Suzuki-Miyaura Cross-Coupling Reactions of Unprotected Haloimidazoles", J. Org. Chem., 2014, pp. 8871-8876, vol. 79.

*Primary Examiner* — Kahsay Habte
(74) *Attorney, Agent, or Firm* — Jeffrey P. Bergman; Catherine D. Fitch

(57) ABSTRACT

The present invention is directed to processes for preparing Substituted Tetracyclic Heterocycle Compounds of formula (I): (I) which may be useful as HCV NS5A inhibitors. The present invention is also directed to compounds that may be useful as synthetic intermediates and catalysts in the processes of the invention.

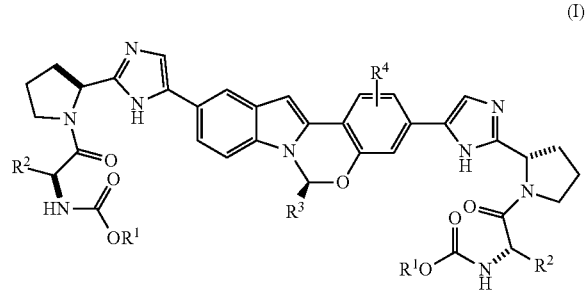

15 Claims, 3 Drawing Sheets

PROCESS FOR PREPARING SUBSTITUTED TETRACYCLIC HETEROCYCLE COMPOUNDS

CROSS-REFERENCE TO RELATED APPLICATIONS

This application is the national stage application under 35 U.S.C. 371 of International Patent Application No. PCT/US2016/35717, filed Jun. 3, 2016, which claims priority to US Provisional Patent Application No. 62/171,039, filed Jun. 4, 2015. Each of the aforementioned applications is incorporated by reference in its entirety.

FIELD OF THE INVENTION

The present invention is directed to processes for preparing Substituted Tetracyclic Heterocycle Compounds which may be useful as HCV NS5A inhibitors. The present invention is also directed to compounds that may be useful as synthetic intermediates and catalysts in the processes of the invention.

BACKGROUND OF THE INVENTION

Various substituted tetracyclic heterocyclic compounds are inhibitors of the HCV NS5A enzyme. Included in these heterocycles are those related to Compound A, as defined and described below. These compounds and pharmaceutically acceptable salts thereof may be useful in the treatment or prophylaxis of infection by HCV and in the treatment, prophylaxis, or delay in the onset or progression of HCV infection. Representative tetracyclic heterocyclic compounds that may be useful for treating HCV infection are described, for example, in US Patent Publication No. US20120083483 and International Patent Publication Nos. WO14/110,705 and WO 2014/110,706. Among the compounds disclosed in WO14/110,705 is dimethyl ((2S,2'S)-((2S,2'S)-2,2'-(5,5'-((S)-6-(2-cyclopropylthiazol-5-yl)-1-fluoro-6H-benzo[5,6][1,3]oxazino[3,4-a]indole-3,10-diyl)bis(1H-imidazole-5,2-diyl))bis(pyrrolidine-2,1-diyl))bis(3-methyl-1-oxobutane-2,1-diyl))dicarbamate, hereinafter referred to as Compound A. Compound A is a known inhibitor of HCV NS5A. The structure of Compound A is as follows:

Compound A

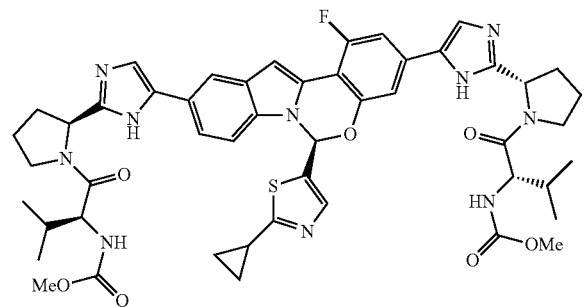

International Publication Number WO14/110,705 discloses methodology that can be used to prepare Compound A and related tetracyclic HCV NS5A inhibitors. This general methodology is illustrated immediately below:

The methods described in US Patent Publication No. US20120083483 and International Publication Numbers WO14/110,705 and WO14/110,706 are practical routes for the preparation of Compound A and related tetracyclic heterocyclic compounds. Nonetheless, there is always a need for alternative preparative routes which, for example, use reagents that are less expensive and/or easier to handle, consume smaller amounts of reagents, provide a higher yield of product, involve fewer steps, have smaller and/or more eco-friendly waste products, and/or provide a product of higher purity.

Unlike the disclosed methods for making tetracyclic HCV NS5A inhibitors described in US Patent Publication No. US20120083483 and International Publication Numbers WO14/110,705 and WO14/110,706 the process of the present invention employs fewer steps and provides an improved yield of Compound A and related NS5A inhibitors.

SUMMARY OF THE INVENTION

The present invention is directed to a process for preparing Substituted Tetracyclic Heterocycle Compounds of Formula (I) which may be useful as HCV NS5A inhibitors. More particularly, the present invention includes a process (alternatively referred to herein as Process P) for preparing a compound of Formula I:

(I)

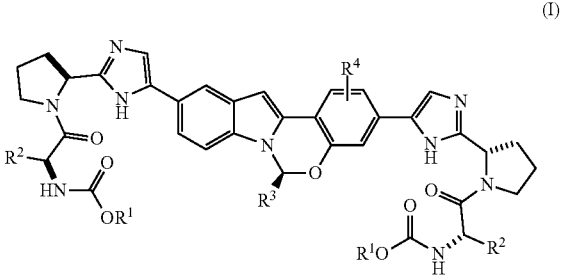

or a pharmaceutically acceptable salt thereof,
wherein said process comprises:
(A) contacting a compound of Formula II:

(II)

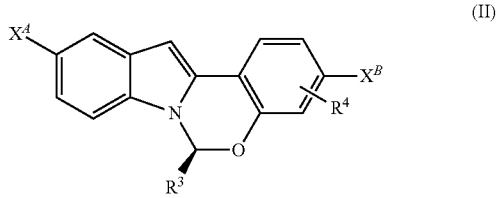

or a salt thereof, with bis(pinacoloato)diboron in the presence of a base, a transition metal catalyst, and an optional phosphorus ligand source, in an organic solvent A, for a time and at a temperature sufficient to provide an intermediate compound of Formula III:

(III)

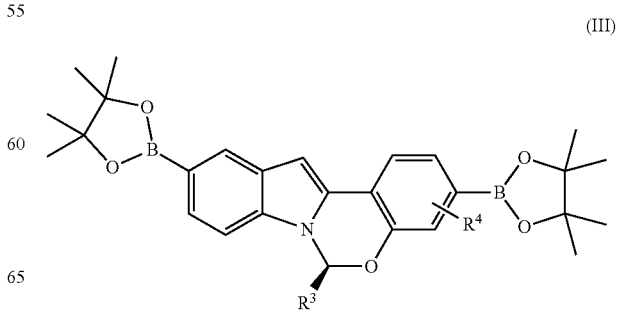

and (B) contacting the intermediate compound of formula III with a compound of formula IV:

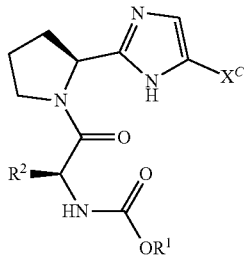

in the presence of a base, a transition metal catalyst, an optional organic acid, and an optional phosphorus ligand source, in an organic solvent B, for a time and at a temperature sufficient to provide the compound of formula (I), wherein organic solvent A and organic solvent B are each independently selected from dimethylacetamide, toluene, acetonitrile, N,N-dimethylformamide, tetrahydrofuran, 2-methyl tetrahydrofuran, CPME, isopropanol, ethanol, ethyl acetate, water, isopropyl acetate and dimethoxyethane, and mixtures thereof, and wherein:

$X^A$ is selected from Br, Cl, I and —OTf;
$X^B$ is selected from Br, Cl, I and —OTf;
$X^C$ is selected from Br, Cl, I and —OTf;
each occurrence of $R^1$ is independently selected from $C_1$-$C_6$ alkyl, $C_3$-$C_7$ cycloalkyl and $C_6$-$C_{10}$ aryl;
each occurrence of $R^2$ is independently selected from $C_1$-$C_6$ alkyl, $C_3$-$C_7$ cycloalkyl, 3 to 7-membered monocyclic heterocycloalkyl and $C_6$-$C_{10}$ aryl;
$R^3$ is selected from $C_1$-$C_6$ alkyl, $C_3$-$C_7$ cycloalkyl, $C_6$-$C_{10}$ aryl, 5 or 6-membered monocyclic heteroaryl and 9 or 10-membered bicyclic heteroaryl, wherein said $C_3$-$C_7$ cycloalkyl group, said $C_6$-$C_{10}$ aryl group, said 5 or 6-membered monocyclic heteroaryl group or said 9 or 10-membered bicyclic heteroaryl group can be optionally substituted with up to three groups, each independently selected from $C_1$-$C_6$ alkyl and $C_3$-$C_7$ cycloalkyl; and
$R^4$ represents up to 3 optional phenyl group substituents, which can be the same or different and are each independently selected from $C_1$-$C_6$ alkyl, —O—$C_1$-$C_6$ alkyl, halo, $C_1$-$C_6$ haloalkyl or —CN.

Other embodiments, aspects and features of the present invention are either further described in or will be apparent from the ensuing description, examples, and appended claims.

DETAILED DESCRIPTION OF THE INVENTION

The present invention is directed to a process for preparing Substituted Tetracyclic Heterocycle Compounds of Formula (I) which may be useful as HCV NS5A inhibitors. One aspect of the present invention is the process comprising Steps A and B as set forth above in the Summary of the Invention (i.e., Process P).

Definitions and Abbreviations

The term "$C_1$-$C_6$ alkyl" as used herein, refers to an aliphatic hydrocarbon group, having from 1 to 6 carbon atoms wherein one of its hydrogen atoms is replaced with a bond. A $C_1$-$C_6$ alkyl group may be straight or branched and contain. Non-limiting examples of $C_1$-$C_6$ alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. A $C_1$-$C_6$ alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH (alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, a $C_1$-$C_6$ alkyl group is linear. In another embodiment, a $C_1$-$C_6$ alkyl group is branched. Unless otherwise indicated, a $C_1$-$C_6$ alkyl group is unsubstituted.

The term "$C_6$-$C_{10}$ aryl" refers to phenyl and naphthyl. In one embodiment, an aryl group is phenyl.

The term "3 to 7-membered cycloalkyl" refers to a non-aromatic monocyclic ring system comprising from about 3 to about 7 ring carbon atoms. Examples of "3 to 7-membered cycloalkyls include cyclopropyl, cyclobutyl, cyclopentyl, cyclohexyl and cycloheptyl. A 3 to 7-membered cycloalkyl group can be optionally substituted with one or more "ring system substituents" which may be the same or different, and are as defined herein below. In one embodiment, a 3 to 7-membered cycloalkyl group is unsubstituted. A ring carbon atom of a 3 to 7-membered cycloalkyl may be functionalized as a carbonyl group. An illustrative example of such a 3 to 7-membered cycloalkyl (also referred to herein as a "cycloalkanoyl" group) includes, but is not limited to, cyclobutanoyl:

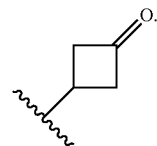 [SMILES: *C1CC(=O)C1]

The term "halo" as used herein, refers to fluorine, chlorine, bromine and iodine (alternatively referred to as fluoro, chloro, bromo, and iodo).

The term "5 or 6-membered monocyclic heteroaryl," as used herein, refers to an aromatic monocyclic ring system comprising about 5 to about 6 ring atoms, wherein from 1 to 4 of the ring atoms is independently O, N or S and the remaining ring atoms are carbon atoms. A 5 or 6-membered monocyclic heteroaryl group can be optionally substituted by one or more "ring system substituents" which may be the same or different, and are as defined herein below. A 5 or 6-membered monocyclic heteroaryl group is joined via a ring carbon atom, and any nitrogen atom of a heteroaryl can be optionally oxidized to the corresponding N-oxide. The term "5 or 6-membered monocyclic heteroaryl" also encompasses a 5 or 6-membered monocyclic heteroaryl group, as defined above, which is fused to a benzene ring. Non-limiting examples of 5 or 6-membered monocyclic heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, benzofurazanyl, indolyl, azaindolyl, benzimidazolyl, benzothienyl, imidazolyl, benzimidazolyl, thienopyridyl, thienopyrimidyl, pyrrolopyridyl, imidazopyridyl, isoquinolinyl, 1,2,4-triazinyl, benzothiazolyl and the like, and all isomeric forms thereof. Unless otherwise indicated, a 5 or 6-membered monocyclic heteroaryl group is unsubstituted.

The term "9 or 10-membered bicyclic heteroaryl," as used herein, refers to an aromatic bicyclic ring system comprising about 9 to about 10 ring atoms, wherein from 1 to 4 of the ring atoms is independently O, N or S and the remaining ring atoms are carbon atoms. A 9 or 10-membered bicyclic heteroaryl group can be optionally substituted by one or more "ring system substituents" which may be the same or different, and are as defined herein below. A 9 or 10-membered bicyclic heteroaryl group is joined via a ring carbon atom, and any nitrogen atom of a heteroaryl can be optionally oxidized to the corresponding N-oxide. Non-limiting examples of 9 or 10-membered bicyclic heteroaryls include and the like, and all isomeric forms thereof. Unless otherwise indicated, a 9 or 10-membered bicyclic heteroaryl group is unsubstituted.

Unless expressly stated to the contrary in a particular context, any of the various cyclic rings and ring systems described herein may be attached to the rest of the compound of which they are a part at any ring atom (i.e., any carbon atom or any heteroatom) provided that a stable compound results.

Unless expressly stated to the contrary, all ranges cited above are inclusive; i.e., the range includes the values for the upper and lower limits of the range as well as all values in between.

When any variable occurs more than one time in a compound involved in the process of the invention (e.g., $R^1$ or $R^2$), its definition on each occurrence is independent of its definition at every other occurrence. Also, combinations of substituents and/or variables are permissible only if such combinations result in a stable compound.

Unless expressly stated to the contrary, substitution by a named substituent is permitted on any atom in a ring (e.g., cycloalkyl, aryl, or heteroaryl) provided such ring substitution is chemically allowed and results in a stable compound.

In reference to the compounds used as reactants or reagents in the process of the invention (e.g., Compounds of Formula (II), (III), and (IV)), a "stable" compound is one whose structure and properties remain or can be caused to remain essentially unchanged for a period of time sufficient to allow its use in the process of the invention so as to achieve the preparation of Compound of Formula (I). In reference to Compound of Formula (I), a "stable" compound is a compound which can be prepared in accordance with the process of the present invention and then isolated and whose structure and properties remain or can be caused to remain essentially unchanged for a period of time sufficient to allow use of the compound for its intended purpose; e.g., for the therapeutic administration to a subject who has HCV infection.

The following abbreviations are used below and have the following meanings: Ac is acetate, ACN or MeCN is acetonitrile, Ad is adamantyl, Amphos is bis(di-tert-butyl(4-dimethylaminophenyl) phosphine), Boc is t-butoxycarbonyl, BrettPhos is 2-(Dicyclohexylphosphino)3,6-dimethoxy-2',4',6'-triisopropyl-1,1'-biphenyl, t-Bu is tertiary butyl, n-Bu is n-butyl, n-BuLi is n-butyllithium, Celite is diatomaceous earth, CPME is cyclopentyl methyl ether, CSA is camphorsulfonic acid, Cuno-3-carbon is activated carbon, Darco G-60 is activated charcoal, DBA and dba are dibenzylidene acetone, DBDTF is 1,1'-Bis(di-tert-butylphosphino)ferrocene, DCDMH is 1,3-Dichloro-5,5-dimethyl hydantoin, DCM is dichloromethane, DENEB is [(S,S)—N-[2-(4-methylbenzyloxy)ethyl]-N-(p-toluenesulfonyl)-1, 2-diphenylethylenediamine], DMAc is dimethylacetamide, D-DTTA is di-para-O-toluoyl-D-tartaric acid, DMA is N,N-dimethylacetamide, DME is dimethoxyethane, DMF is N,N-dimethylformamide, DMSO is dimethylsulfoxide, EDC is 1-ethyl-3-(3-dimethylaminopropyl) carbodiimide hydrochloride, Et is ethyl, EtOAc is ethyl acetate, EtOH is ethanol, HOBt is hydroxybenzotriazole, HOPO is octadentate hydroxypyridinonate, HPLC is high performance liquid chromatography, IPAC is isopropyl acetate, i-PrOH is isopropanol, LCAP is Laboratory of Pharmaceutical Analytical Chemistry, Me is methyl, Me is methyl, 2-Me-THF is 2-methyltetrahydrofuran, MeOH is methanol, Moc is N-methoxycarbonyl, Moc-valine is N-methoxycarbonyl-L-valine, Ms is mesyl or methanesulfonyl, MTBE is methyl tert-butyl ether, NMR is nuclear magnetic resonance, $PCy_3$ is tricyclohexyl phosphine, POP is pyrophosphate, (R) QuinoxP(R) is (R,R)-(−)-2,3-Bis(tert-butylmethylphosphino) quinoxaline, Piv is pivalate, SFC is supercritical fluid chromatography, SPhos is 2-Dicyclohexylphosphino-2',6'-dimethoxybiphenyl, TBHP is t-butyl hydroperoxide, TFA is trifluoroacetic acid, THF is tetrahydrofuran, TLC is thin-layer chromatography, tol is toluene and XPhos is 2-dicyclohexylphosphino-2',4',6'-triisopropylbiphenyl.

THE PROCESSES OF THE PRESENT INVENTION

Figure 1:
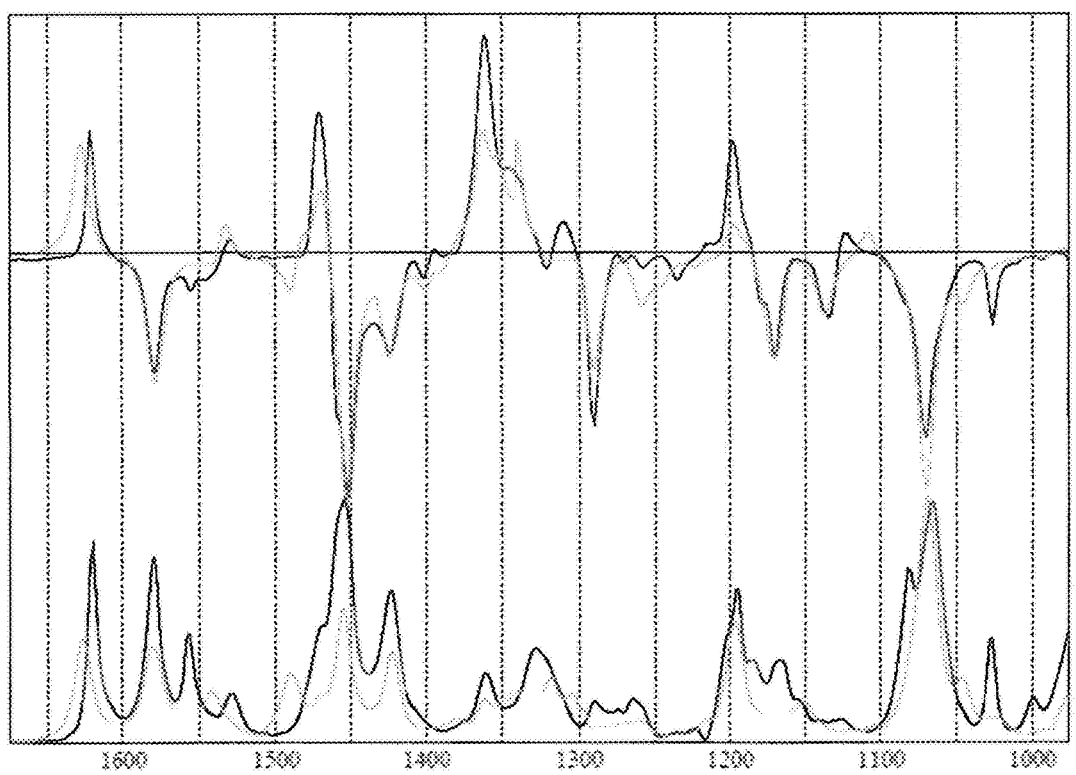
FIG. 1 shows the IR spectrum (lower frame) and experimental vibrational circular dichroism (VCD) spectrum (upper frame) of compound 3F. The black lines represent the observed spectra and the red lines indicate the calculated spectra for compound 3F. The observed VCD spectrum of 3F compares better with the Boltzmann population-weighted calculated spectrum of the (S) configuration for the monomer over the range 1000-1650 cm-1 and confirms the (S) configuration for compound 3F. This set of overlays was generated by a development version of an in-house spectral comparison tool.
Figure 2:
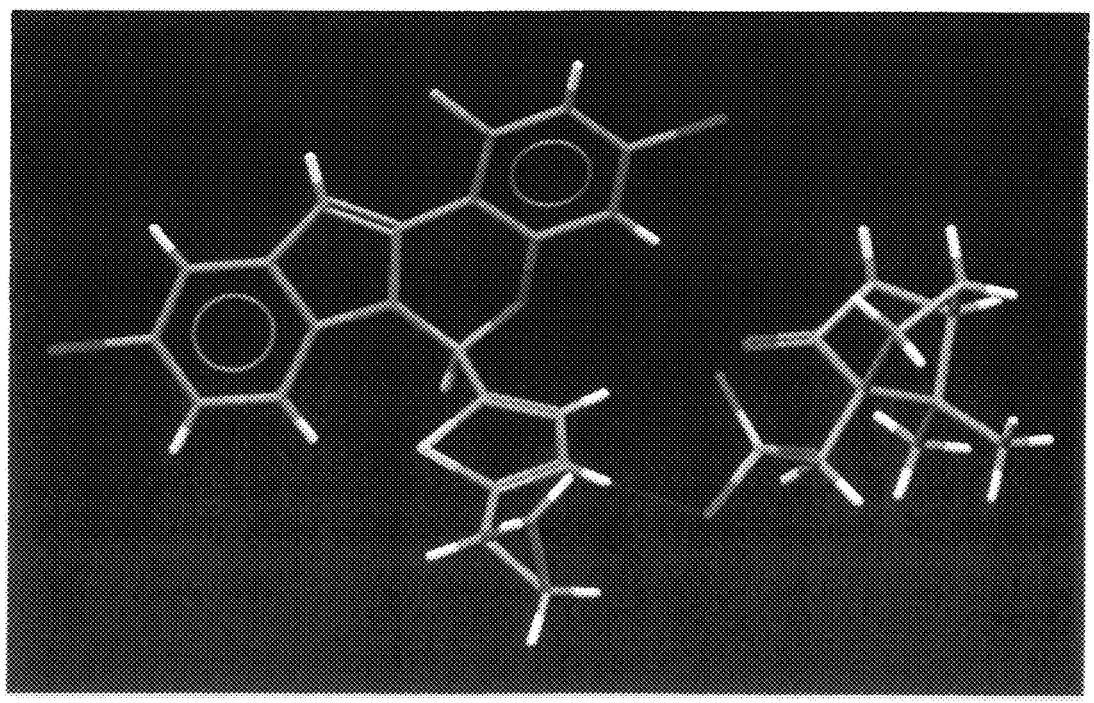
FIG. 2 shows the x-ray structure of the CSA salt of compound 1A.

The present invention is directed to a process for preparing Substituted Tetracyclic Heterocycle Compounds of Formula (I) which may be useful as HCV NS5A inhibitors. One aspect of the present invention is the process comprising Steps A and B as set forth above in the Summary of the Invention (i.e., Process P).

In another aspect, the present invention provides each individual step of Process P as a separate and individual embodiment (e.g., in one embodiment the present invention provides the process illustrated in Step A of Process P; in another embodiment the present invention provides the process illustrated in Step B of Process P).

In one embodiment, for Process P, the base used in Step A is an acetate or pivalate base.

In another embodiment, for Process P, the base used in Step A is an alkali metal acetate base.

In another embodiment, for Process P, the optional phosphate ligand referred to in Step A is present.

In one embodiment, for Process P, the base used in Step B is a carbonate or phosphate base.

In another embodiment, for Process P, the base used in Step A is an alkali metal carbonate base.

In another embodiment, for Process P, the optional phosphate ligand referred to in Step B is present.

In one embodiment, for process P, organic solvents A and B are each independently selected from water, 2-Me THF, DME or a mixture thereof.

In one embodiment, for Process P:

Step A is conducted at a temperature in a range of from about 40° C. to about 110° C.;

the organic solvent A used in step A is selected from tetrahydrofuran, 2-methyl tetrahydrofuran, water, dimethoxyethane, isopropyl acetate, and mixtures thereof;

the base used in Step A is an acetate or pivalate base;

the transition metal catalyst used in Step A is selected from $Pd_2dba_3$, $Pd(OAc)_2$ and $PdCl_2$;

the optional phosphorus ligand used in Step A is present and is selected from n-Bu(Ad)$_2$P, Amphos, n-BuP(t-Bu)$_2$-HBF$_4$, XPhos, SPhos, BrettPhos, DTBPF, PCy$_3$ and P(t-Bu)$_3$;

Step B is conducted at a temperature in a range of from about 50° C. to about 120° C.;

the organic solvent B used in step B is selected from tetrahydrofuran, 2-methyl tetrahydrofuran, water, dimethoxyethane, isopropyl acetate, and mixtures thereof;

the base used in Step B is a carbonate or phosphate base;

the transition metal catalyst used in Step B is selected from $Pd_2dba_3$, $Pd(OA_c)_2$ and $PdCl_2$; and the optional phosphorus ligand used in Step B is present and is selected from n-Bu(Ad)$_2$P, Amphos, n-BuP(t-Bu)$_2$-HBF$_4$, XPhos, SPhos, BrettPhos, DTBPF, PCy$_3$ and P(t-Bu)$_3$.

In another embodiment, for Process P:

Step A is conducted at a temperature in a range of from about 50° C. to about 100° C.;

the organic solvent A used in step A is selected from tetrahydrofuran, 2-methyl tetrahydrofuran, dimethoxyethane, water, and mixtures thereof;

the base used in Step A is an alkali metal acetate base;

the transition metal catalyst used in Step A is $Pd(OAc)_2$;

the optional phosphorus ligand used in Step A is present and is selected from XPhos, SPhos and BrettPhos;

Step B is conducted at a temperature in a range of from about 65° C. to about 90° C.;

the organic solvent B used in step B is selected from tetrahydrofuran, 2-methyl tetrahydrofuran, water, and mixtures thereof;

the base used in Step B is an alkali metal carbonate base;

the transition metal catalyst used in Step B is $Pd(OAc)_2$; and the optional phosphorus ligand used in Step B is present and is selected from XPhos, SPhos and BrettPhos.

In another embodiment, for Process P:

Step A is conducted at a temperature in a range of from about 50° C. to about 100° C.;

the organic solvent A used in step A is a mixture of 2-methyl tetrahydrofuran and water;

the acetate or pivalate base used in Step A is KOAc;

the transition metal catalyst used in Step A is $Pd(OAc)_2$;

the optional phosphorus ligand used in Step A is present and is XPhos;

Step B is conducted at a temperature in a range of from about 50° C. to about 90° C.;

the organic solvent B used in step B is a mixture of 2-methyl tetrahydrofuran and water;

the carbonate acetate or pivalate base used in Step B is potassium carbonate;

the transition metal catalyst used in Step B is $Pd(OAc)_2$; and the optional phosphorus ligand used in Step B, is present and is XPhos.

In one embodiment, for Process P, each occurrence of $R^1$ and $R^2$ is independently $C_1$-$C_6$ alkyl and $R^3$ is 5 or 6-membered heteroaryl or $C_6$-$C_{10}$ aryl, wherein $R^3$ can be optionally substituted with a group selected from $C_1$-$C_6$ alkyl and $C_3$-$C_7$ cycloalkyl.

In another embodiment, for Process P, each occurrence of $R^1$ is methyl and each occurrence of $R^2$ is isopropyl.

In another embodiment, for Process P, each occurrence of $R^1$ is methyl, each occurrence of $R^2$ is isopropyl and $R^3$ is phenyl.

In another embodiment, for Process P, $R^3$ is phenyl, thiazolyl or thiophenyl, each of which can be optionally substituted with a group selected from $C_1$-$C_6$ alkyl and $C_3$-$C_7$ cycloalkyl.

In still another embodiment, for Process P, each occurrence of $R^1$ is methyl, each occurrence of $R^2$ is isopropyl and $R^3$ is phenyl, thiazolyl or thiophenyl, each of which can be optionally substituted with a group selected from $C_1$-$C_6$ alkyl and $C_3$-$C_7$ cycloalkyl.

In one embodiment, for Process P, $X^C$ is Cl.

In another embodiment, for Process P, $X^C$ is Br.

In another embodiment, for Process P, $R^4$ is —F.

In still another embodiment, for Process P, $R^4$ is absent.

In one embodiment, for Process P, the compound of formula (I) being prepared is Compound A:

Compound A

In one embodiment, for Process P, the compound of formula (I) being prepared is Compound B:

Compound B

In one embodiment, for Process P, the compound of formula (I) being prepared is Compound C:

Compound C

In one embodiment of Process P, the invention provides a process for preparing Compound A:

Compound A

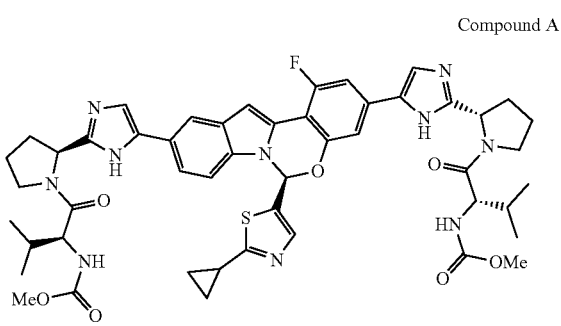 [SMILES: COC(=O)N[C@H](C(=O)N1CCC[C@H]1c1ncc(-c2cc(F)c3c(c2)O[C@@H](c2cnc(C4CC4)s2)n2c-3cc3cc(-c4cnc([C@@H]5CCCN5C(=O)[C@@H](NC(=O)OC)C(C)C)[nH]4)ccc32)[nH]1)C(C)C]

wherein said process comprises the steps:
(A) contacting a compound of Formula IIa:

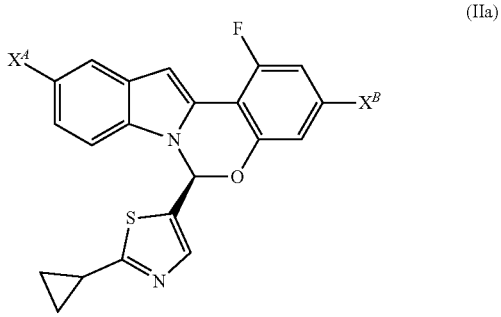
(IIa)

or a salt thereof, with bis(pinacoloato)diboron in the presence of an acetate base, a palladium catalyst, and a phosphorus ligand source, in a mixture of water and an organic solvent A, for a time and at a temperature sufficient to provide an intermediate compound of Formula IIIa:

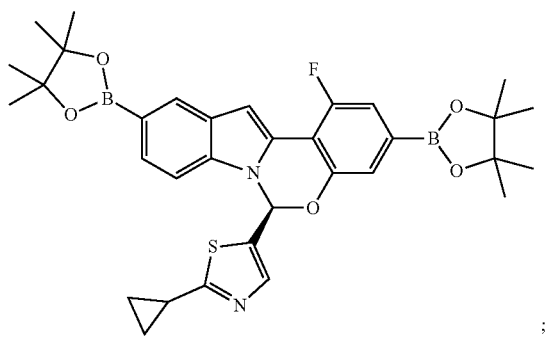
(IIIa)

and
(B) contacting the intermediate compound of formula IIIa with a compound of formula IVa:

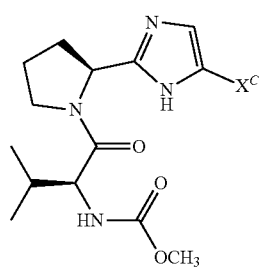
(IVa)

in the presence of a base and a palladium catalyst, and a phosphorus ligand source, in a mixture of water and organic solvent B, for a time and at a temperature sufficient to provide compound A, wherein organic solvents A and B are each independently selected from tetrahydrofuran, 2-methyl tetrahydrofuran, dimethoxyethane, toluene, ethyl acetate and isopropyl acetate; $X^A$ is selected from Br, Cl and I; $X^B$ is selected from Br, Cl and I; and $X^C$ is selected from Br, Cl and I.

In one embodiment, the present invention provides a process for preparing a compound of Formula III ("Process A"):

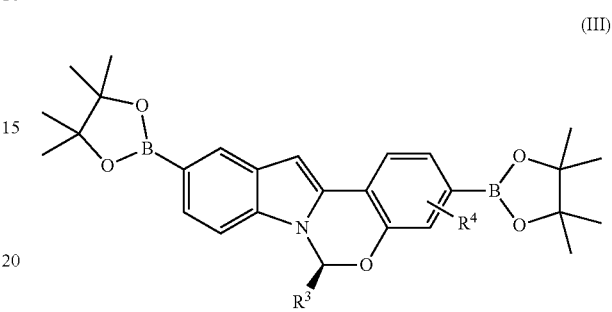
(III)

wherein said process comprises contacting a compound of Formula II:

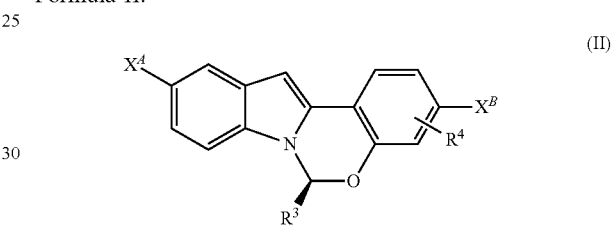
(II)

or a salt thereof, with bis(pinacoloato)diboron in the presence of a base, a transition metal catalyst, and optionally in the presence of a phosphorus ligand source, in an organic solvent A, for a time and at a temperature sufficient to provide the compound of Formula III, wherein organic solvent A is selected from dimethylacetamide, toluene, acetonitrile, N,N-dimethylformamide, tetrahydrofuran, 2-methyl tetrahydrofuran, CPME, isopropanol, ethanol, ethyl acetate, water, isopropyl acetate and dimethoxyethane, and mixtures thereof, and wherein:

$X^A$ is selected from Br, Cl, I and —OTf;
$X^B$ is selected from Br, Cl, I and —OTf;
$R^3$ is selected from $C_1$-$C_6$ alkyl, $C_3$-$C_7$ cycloalkyl, $C_6$-$C_{10}$ aryl, 5 or 6-membered monocyclic heteroaryl and 9 or 10-membered bicyclic heteroaryl, wherein said $C_3$-$C_7$ cycloalkyl group, said $C_6$-$C_{10}$ aryl group, said 5 or 6-membered monocyclic heteroaryl group or said 9 or 10-membered bicyclic heteroaryl group can be optionally substituted with up to three groups, each independently selected from $C_1$-$C_6$ alkyl and $C_3$-$C_7$ cycloalkyl; and
$R^4$ represents up to 3 optional phenyl group substituents, which can be the same or different and are each independently selected from $C_1$-$C_6$ alkyl, —O—$C_1$-$C_6$ alkyl, halo, $C_1$-$C_6$ haloalkyl or —CN.

In another embodiment, for Process A, the base used in Step A is an alkali metal acetate base.

In another embodiment, for Process A, the optional phosphate ligand referred to in Step A is present.

In one embodiment, for Process A, the base used is a carbonate or phosphate base.

In another embodiment, for Process A, the base used is an alkali metal carbonate base or phosphate base.

In another embodiment, for Process A, the optional phosphate ligand is present.

In one embodiment, for Process A:
said process is conducted at a temperature in a range of from about 50° C. to about 100° C.;
the organic solvent A is selected from tetrahydrofuran, 2-methyl tetrahydrofuran, dimethoxyethane, water, and mixtures thereof;
the acetate or pivalate base used is an alkali metal acetate base;
the transition metal catalyst used is Pd(OAc)$_2$; and
the optional phosphorus ligand is present and is selected from XPhos, SPhos and BrettPhos.

In one embodiment, for Process A, R$^3$ is 5 or 6-membered monocyclic heteroaryl or C$_6$-C$_{10}$ aryl, wherein R$^3$ can be optionally substituted with a group selected from C$_1$-C$_6$ alkyl and C$_3$-C$_7$ cycloalkyl.

In another embodiment, for Process A, R$^4$ represents one halo substituent.

In another embodiment, for Process A, R$^4$ represents one F substituent.

In another embodiment, for Process A, R$^4$ is —F.

In still another embodiment, for Process A, R$^4$ is absent.

In another embodiment, for Process A, X$^A$ and X$^B$ the same and are each Br or Cl.

In one embodiment, for Process A, the compound of formula (III) being prepared

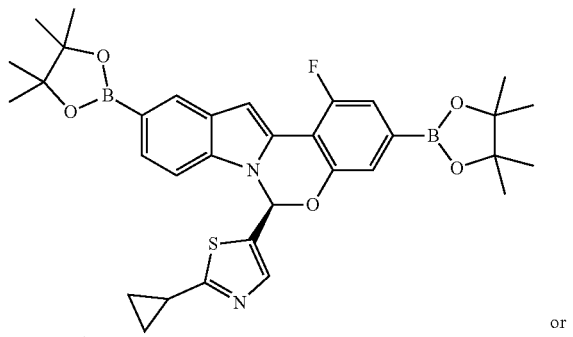

or

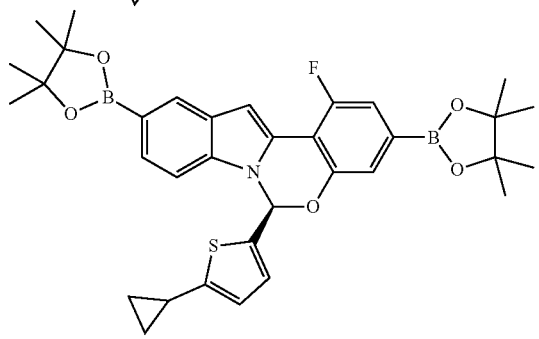

In one embodiment, the present invention provides a process for preparing a compound of Formula I ("Process B"):

(I)

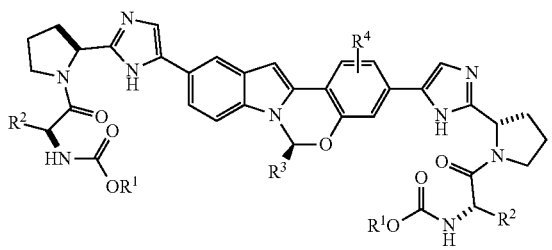

or a pharmaceutically acceptable salt thereof, wherein said process comprises contacting an intermediate compound of formula III:

(III)

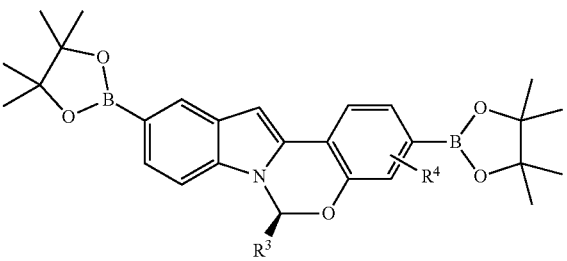

with a compound of formula IV:

(IV)

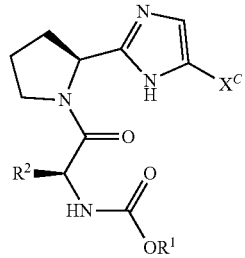

in the presence of a carbonate base or phosphate base and a transition metal catalyst, and optionally in the presence of a phosphorus ligand source, in a mixture of water and organic solvent B, for a time and at a temperature sufficient to provide the compound of formula (I), wherein organic solvent B is selected from dimethylacetamide, toluene, acetonitrile, N,N-dimethylformamide, tetrahydrofuran, 2-methyl tetrahydrofuran, CPME, isopropanol, ethanol, ethyl acetate, water, isopropyl acetate and dimethoxyethane, and mixtures thereof, and wherein:

X$^C$ is selected from Br, Cl, I and —OTf;

each occurrence of R$^1$ is independently selected from C$_1$-C$_6$ alkyl, C$_3$-C$_7$ cycloalkyl and C$_6$-C$_{10}$ aryl;

each occurrence of R$^2$ is independently selected from C$_1$-C$_6$ alkyl, C$_3$-C$_7$ cycloalkyl, 3 to 7-membered monocyclic heterocycloalkyl and C$_6$-C$_{10}$ aryl;

R$^3$ is selected from C$_1$-C$_6$ alkyl, C$_3$-C$_7$ cycloalkyl, C$_6$-C$_{10}$ aryl, 5 or 6-membered monocyclic heteroaryl and 9 or 10-membered bicyclic heteroaryl, wherein said C$_3$-C$_7$ cycloalkyl group, said C$_6$-C$_{10}$ aryl group, said 5 or 6-membered monocyclic heteroaryl group or said 9 or 10-membered bicyclic heteroaryl group can be optionally substituted with up to three groups, each independently selected from C$_1$-C$_6$ alkyl and C$_3$-C$_7$ cycloalkyl; and R$^4$ represents up to 3 optional phenyl group substituents, which can be the same or different and are each independently selected from C$_1$-C$_6$ alkyl, —O—C$_1$-C$_6$ alkyl, halo, C$_1$-C$_6$ haloalkyl or —CN.

In one embodiment, for Process B, the base used is a carbonate or phosphate base.

In another embodiment, for Process B, the base used is an alkali metal carbonate base.

In another embodiment, for Process B, the optional phosphate ligand is present.

In one embodiment, for Process B:
said process is conducted at a temperature in a range of from about 50° C. to about 90° C.;
the organic solvent B used is selected from tetrahydrofuran, 2-methyl tetrahydrofuran, dimethoxyethane, water, and mixtures thereof;
the base used is an alkali metal carbonate base;
the transition metal catalyst used is Pd(OAc)$_2$; and the optional phosphorus ligand is present and is selected from XPhos, SPhos and BrettPhos.

In one embodiment, for Process B, each occurrence of $R^1$ and $R^2$ is independently $C_1$-$C_6$ alkyl and $R^3$ is 5 or 6-membered heteroaryl or $C_6$-$C_{10}$ aryl, wherein $R^3$ can be optionally substituted with a group selected from $C_1$-$C_6$ alkyl and $C_3$-$C_7$ cycloalkyl.

In another embodiment, for Process B, each occurrence of $R^1$ is methyl and each occurrence of $R^2$ is isopropyl.

In another embodiment, for Process B, $R^3$ is phenyl, thiazolyl or thiophenyl, each of which can be optionally substituted with a group selected from $C_1$-$C_6$ alkyl and $C_3$-$C_7$ cycloalkyl.

In still another embodiment, for Process B, each occurrence of $R^1$ is methyl, each occurrence of $R^2$ is isopropyl and $R^3$ is phenyl, thiazolyl or thiophenyl, each of which can be optionally substituted with a group selected from $C_1$-$C_6$ alkyl and $C_3$-$C_7$ cycloalkyl.

In one embodiment, for Process B, $X^C$ is Cl.

In another embodiment, for Process B, $X^C$ is Br.

In another embodiment, for Process B, $R^4$ is —F.

In still another embodiment, for Process B, $R^4$ is absent.

In one embodiment, for Process B, the compound of formula (I) being prepared is Compound A:

Compound A

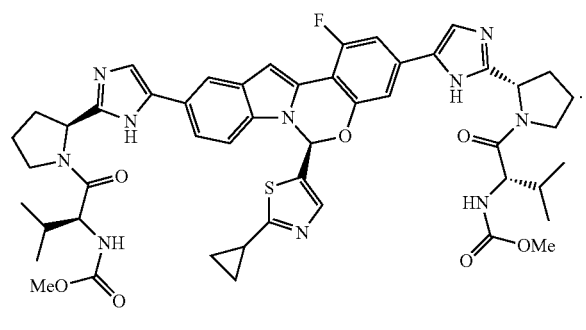

In one embodiment, for Process B, the compound of formula (I) being prepared is Compound B:

Compound B

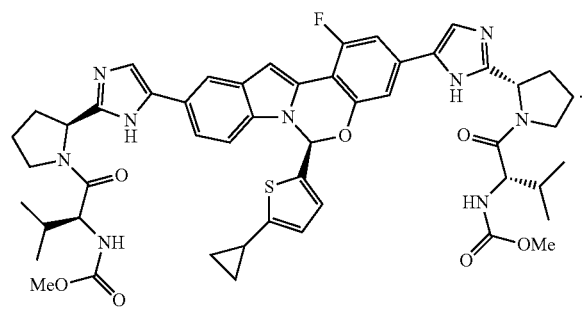

In one embodiment, for Process B, the compound of formula (I) being prepared is Compound C:

Compound C

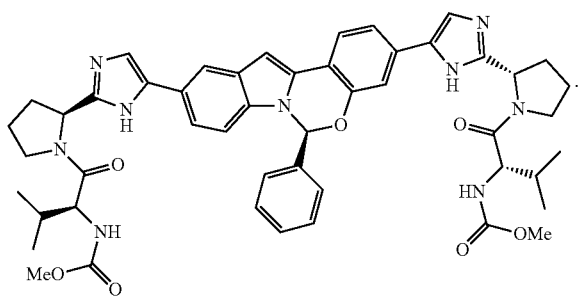

In one embodiment, the present invention provides the bis-mandelate salt of Compound A:

Compound A

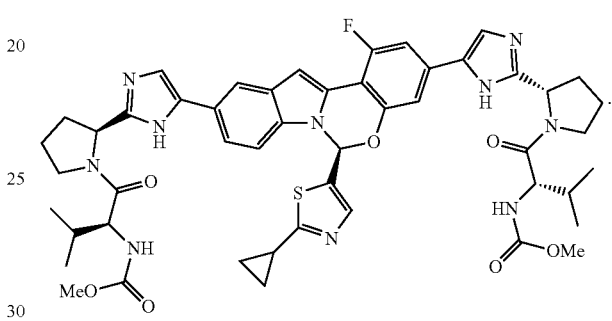

In one embodiment, the present invention provides the ethanol solvate of Compound A:

Compound A

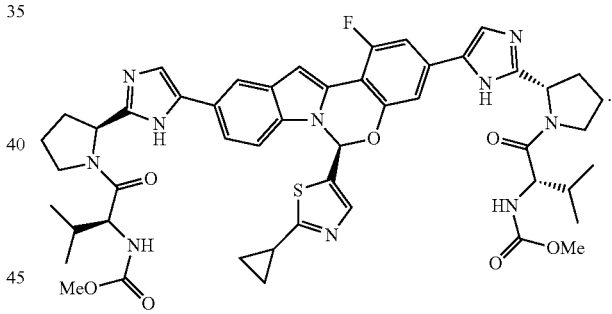

In another embodiment, the present invention provides the CSA salt of Compound 1A:

1A

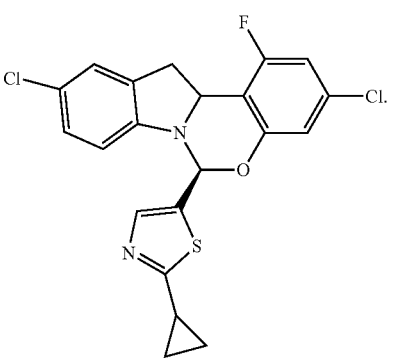

In one embodiment, the present invention provides a compound having the formula:

(III)

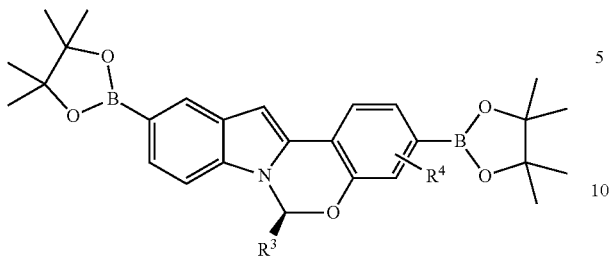

or a salt thereof, wherein:

R³ is C₁-C₆ alkyl, C₃-C₇ cycloalkyl, C₆-C₁₀ aryl, 5 or 6-membered monocyclic heteroaryl or 9 or 10-membered bicyclic heteroaryl, wherein said C₃-C₇ cycloalkyl group, said C₆-C₁₀ aryl group, said 5 or 6-membered monocyclic heteroaryl group or said 9 or 10-membered bicyclic heteroaryl group can be optionally substituted with up to three groups, each independently selected from C₁-C₆ alkyl and C₃-C₇ cycloalkyl; and R⁴ represents up to 3 optional phenyl group substituents, which can be the same or different and are each independently selected from C₁-C₆ alkyl, —O—C₁-C₆ alkyl, halo, C₁-C₆ haloalkyl or —CN.

In another embodiment, the present invention provides a compound having the structure:

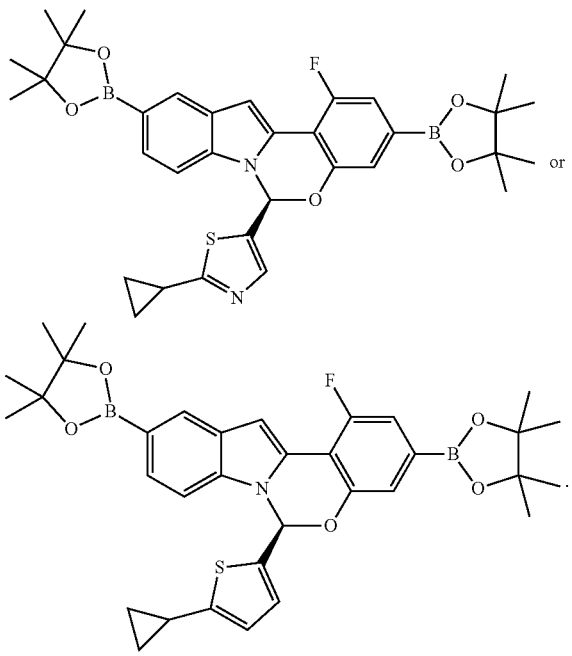

In one embodiment, the present invention provides a compound having the formula:

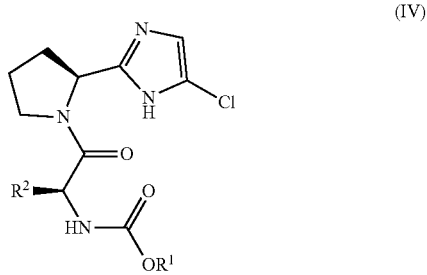

wherein R¹ is selected from C₁-C₆ alkyl, C₃-C₇ cycloalkyl and C₆-C₁₀ aryl and R² is selected from C₁-C₆ alkyl, C₃-C₇ cycloalkyl, 3 to 7-membered monocyclic heterocycloalkyl and C₆-C₁₀ aryl.

In one embodiment, for the compound of formula (IV), R¹ is C₁-C₆ alkyl and R² is C₁-C₆ alkyl.

In another embodiment, for the compound of formula (IV), R¹ is methyl and R² is isopropyl.

In one embodiment, any step of any of the processes described herein can be conducted in any organic solvent.

EXAMPLES

General Methods

Solvents, reagents, and intermediates that are commercially available were used as received. Reagents and intermediates that are not commercially available were prepared in the manner as described below. ¹H NMR spectra were obtained on a Bruker Avance 500 (500 MHz) and are reported as ppm downfield from Me₄Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% CH₃CN, 5 minutes—95% CH₃CN, 5-7 minutes—95% CH₃CN, 7 minutes—stop. The retention time and observed parent ion are given. Flash column chromatography on silica gel was performed using pre-packed normal phase silica from Biotage, Inc. or bulk silica from Fisher Scientific. Unless otherwise indicated, flash column chromatography was performed using a gradient elution of hexanes/ethyl acetate, from 100% hexanes to 100% ethyl acetate.

Example 1

Process for Making Compound A

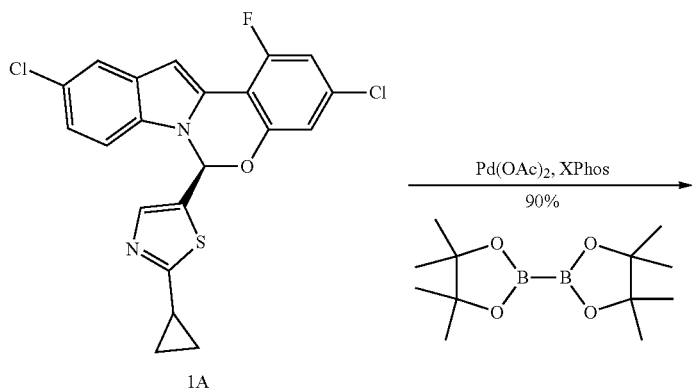

-continued

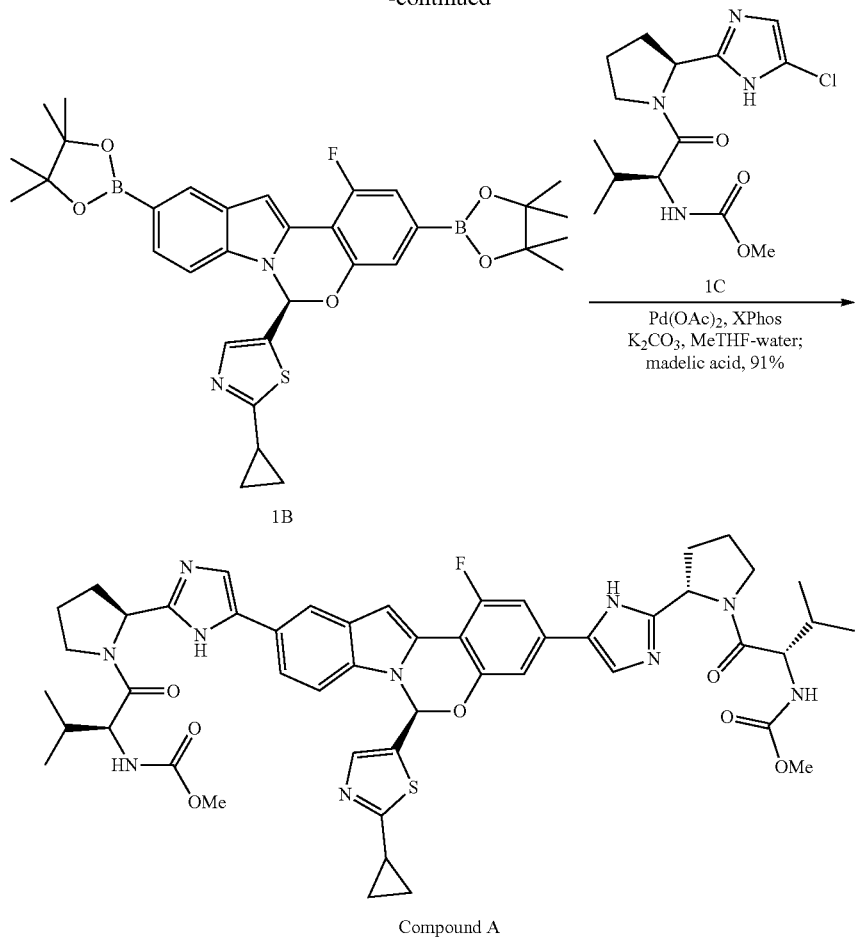

Compound A

Step A—Synthesis of Compound 1B

In a 500 mL 3-necked round-bottomed flask with an overhead stirrer was charged 1A ((S)-CSA salt, 10.0 g, or equivalent amount of the free base), bis(pinacolato)diboron (8.50 g), potassium acetate (8.78 g), and 5-chloroindole (0.46 g) under nitrogen. Degassed 2-Me-THF (130 mL) and water (0.54 mL) were added. In a separate vessel was charged palladium acetate (0.067 g) and Xphos (2-dicyclohexylphosphino-2',4',6'-triisopropylbiphenyl) (0.293 g) and degassed 2-Me-THF (20 mL) under nitrogen, and the mixture was allowed to stir for 30 minutes then added to the flask containing 1A. The mixture was then heated to 75° C., and allowed to age at this temperature for 1 hour or until complete conversion, the allowed to cool to room temperature. Water (30 mL) was added to the mixture, and then layers were separated. The organic layer was washed with 10% brine (30 mL), then treated with Cuno-3-carbon (1.0 g) for about 15 hours. The mixture was filtered through a Celite-pad to remove carbon. The solution was concentrated in vacuo to about approximately 35 mL mixture. Seed crystals were added to initiate the crystallization. The mixture was allowed to age at room temperature for 10 minutes before acetonitrile (105 mL) was added slowly. The resultant slurry was filtered and the collected solid was washed with a mixture of acetonitrile/2-Me-THF (3:7, 30 mL), then dried in a nitrogen stream to provide 1B (8.05 g). $^1$H NMR (CDCl$_3$, 500 MHz), 8.23 (s, 1H), 7.70 (d, J=8.3 Hz, 1H), 7.50 (s, 1H), 7.31 (d, J=9.6 Hz, 1H), 7.29 (d, J=7.1 Hz, 1H), 7.23 (d, J=8.3 Hz, 1H), 7.18 (d, J=3.3 Hz, 1H), 7.10 (s, 1H), 2.15-2.10 (m, 1H), 1.39 (s, 6H), 1.37 (s, 3H), 1.37 (s, 3H), 1.06-1.02 (m, 4H), 1.01-0.95 (m, 4H).

The following complex, 1E, was isolated as an impurity from Step A above:

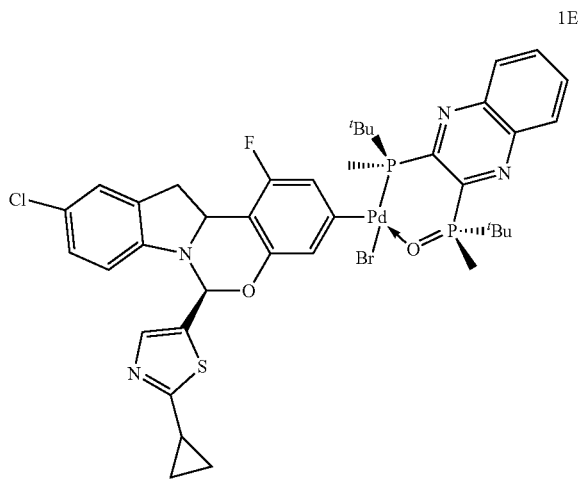

$^{31}$P NMR (202 MHz, toluene-d8) δ 63.7 (P=O), 63.6 (P=O), 25.6 (P) and 25.3 (P) ppm LRMS-ESI m/z calcd. for C$_{39}$H$_{41}$ClFN$_4$O$_2$P$_2$PdS$^+$: 851.11, found 851.35 [M-Br]$^+$.

Step B—Synthesis of Compound A

To a high pressure vessel was charged compound 1B (10.0 g, 16.28 mmol, 1.0 eq), compound 1C (11.5 g, 2.15 eq.), 2-Me-THF (90 mL) and K$_2$CO$_3$ (98 mL, 1 M, 6 eq.). The vessel was degassed. In a second reaction vessel was charged Pd(OAc)$_2$ (0.11 g, 3%) and Xphos (0.58 g, 7.5%), then the second vessel was degassed followed by addition of degassed 2-Me-THF (20 mL). The resulting catalyst/ligand slurry was allowed to age for 2 hours at room temperature under nitrogen atmosphere. It was then transferred to the reaction vessel containing compound 1C and rinsed with degassed 2-Me-THF (10 mL). The resulting reaction mixture was degassed again, and the reaction vessel was sealed and heated at 85 to 90° C. for about 8 hours until >99.5% conversion was reached. The reaction was cooled down to room temperature, and the organic layer was sequentially washed with 10% NaCl solution (18 mL) and 3% NaCl solution (18 mL). The organic layer was then concentrated in vacuo and azeotropically dried via distillation to provide crude product (14.66 g).

The crude product (14.66 g) in 2-Me-THF (135 mL) was charged MeOH (19.4 mL) and tri-n-butylphosphine (2.32 mL). It was heated to 70° C. followed by addition of a solution of (S)-mandelic acid (0.94 g) dissolved in 2-Me-THF (3.87 mL). After aging at 70° C. for several hours, the reaction mixture was cooled to 60° C., and another portion of (S)-mandelic acid (3.06 g) in 2-Me-THF (12.58 mL) was added. The batch was seeded with the mandelate salt of Compound A. A final portion of S-mandelic acid (35.41 g) in 2-Me-THF (22.25 mL) was charged over 4 hours at 60° C. The reaction mixture was gradually cooled to 20° C. over 8 hours and then aged at 20° C. for 1 hour. The slurry was filtered, rinsed with 2-Me-THF (containing 2% wt (S)-mandelic acid). The collected solid was dried at 60° C. to provide the bis-mandelate salt of Compound A as a solid (18.74 g).

The bis-mandelate salt of Compound A (6 g) was mixed with ethyl acetate (48 mL) and water (25.7 mL). To the biphasic mixture was added 2M potassium carbonate solution (6 mL, 2.5 equivalents) over 10 minutes, during which a biphasic solution was generated. The lower aqueous layer was cut away, and the organic layer washed sequentially with 8% brine solution (30 mL) and water (2×30 mL). The organic layer was azeotropically dried via distillation (final solution volume=30 mL). Heptane (66 mL) was charged to an inerted flask. The ethyl acetate stream containing product was added to the heptane over a period of 2 hours. After aging for another 2 hours, the product slurry was filtered, and the wet filter cake was washed with a mixture of heptane (10.8 mL) and EtOAc (2 mL). The solid was dried in vacuo for about 15 hours at 60° C. to provide compound A as its free base (4.40 g, MS: M+H 947.4047). $^1$H NMR (d$_6$-DMSO, 500 MHz) δ (ppm) 8.30 (s, 1 H), 8.22 (br s, 1 H), 8.10 (br s, 1 H), 8.00 (s, 1 H), 7.78 (d, J=8.7 Hz, 1 H), 7.67-7.65 (m, 2 H), 7.52 (br s, 1 H), 7.38 (s, 1 H), 7.31-7.28 (m, 2 H), 7.19 (d, J=3.2 Hz, 1 H), 5.16 (t, J=7.4 Hz, 1 H), 5.14 (t, J=7.4 Hz, 1 H), 4.15-4.11 (m, 2 H), 3.91-3.81 (m, 4 H), 3.55 (s, 6 H), 2.45-2.36 (m, 2 H), 2.26 (m, 1 H), 2.20-2.13 (m, 2 H), 2.13-2.06 (m, 2 H), 2.06-2.00 (m, 4 H), 0.99 (m, 2 H), 0.85-0.77 (m, 14 H). $^{13}$C NMR (d$_6$-DMSO, 126 MHz) δ (ppm) 175.20, 171.21, 171.15, 158.61 (d, J=251.0 Hz), 156.95, 156.94, 150.05, 149.54 (d, J=7.3 Hz), 148.88, 141.37, 133.88, 133.00, 131.11, 130.68, 129.14, 128.78, 125.35, 121.40, 120.38, 118.15, 117.01, 114.18, 111.04, 110.75, 107.30 (d, J=23.4 Hz), 106.67 (d, J=18.2 Hz), 102.94 (d, J=8.6 Hz), 78.46, 57.95, 57.93, 53.06, 52.91, 51.51, 47.16, 47.11, 31.02, 30.95, 29.08, 24.80, 24.75, 19.35, 19.32, 17.74, 13.88, 11.17, 11.05.

Preparation of EtOH Solvate of Compound A

The bis-mandelate salt of Compound A (702 g) was mixed with ethyl acetate (6.3 L) and water (10 L). To the resulting solution was added 0.2M K$_2$CO$_3$ (0.7 L) was added over 10 minutes, followed by another 0.2 eq K$_2$CO$_3$ (15 g K$_2$CO$_3$ in 54 mL water). The aqueous layer was cut away and the organic layer was washed with water (2×2.8 L). The organic layer was concentrated in vacuo and solvent-switched to EtOH (2.7 L). Another 1.5 L of EtOH was added and the solution was heated to 40° C. A product seed slurry (~20 mL of slurry) was added, and the mixture was aged at 40° C. for 3 hours followed by cooling to 2° C. over a period of 8 hours. The batch was filtered and the wet filter cake was washed with 3 L ethanol (2 L+1 L, stored in a freezer overnight), then dried in a vacuum oven to provide the ethanol solvate of Compound A (442 g).

Alternate Process for Making Compound A bis-mandelate Salt (Using Intermediate 1D in Place of 1C):

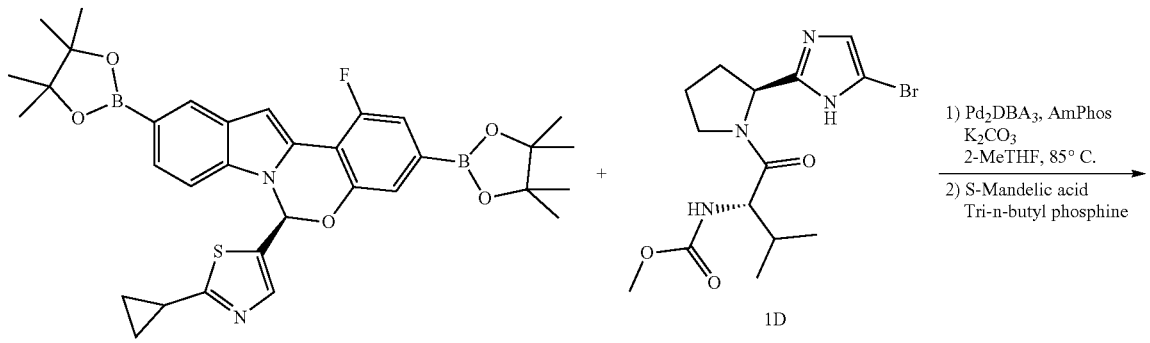

-continued

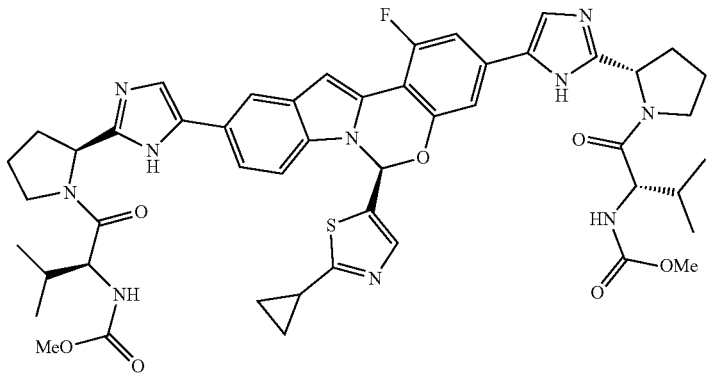

Compound A

A high pressure vessel was charged with 1B (3.0 g, 4.64 mmol, 1.0 eq), 1D (3.72 g, 2.15 eq.), 2-Me-THF (27.0 mL) and $K_2CO_3$ (27.8 mL, 1 M, 6 eq.) and the reaction was degassed. The catalyst/ligand complex was prepared in a second vessel, in which $Pd_2DBA_3$ (0.064 g, 0.070 mmol, 1.5%) and Amphos (0.074 g, 0.278 mmol, 6%) was charged. This second vessel was degassed followed by charging degassed 2-Me-THF (6.0 mL). The resulting catalyst/ligand slurry was allowed to age for 2 hours at room temperature under nitrogen atmosphere, then was transferred to above reaction vessel, rinsed with degassed 2-Me-THF (3.0 mL). The resulting reaction mixture was degassed again, the reaction vessel was sealed and was heated to 85° C. for 14 hours until >99.5% conversion was reached. The reaction was cooled down to room temperature, the aqueous layer was cut. The organic layer was sequentially washed with 10% NaCl solution (9.0 mL), 3% NaCl solution (9.0 mL) and water (9.0 mL). The organic crude was concentrated in vacuo to a final volume of 30.7 mL.

To the concentrated crude was added MeOH (4.39 mL) and tri-n-butylphosphine (0.69 mL, 0.6 eq.). The solution was heated to 60° C. followed by addition of S-mandelic acid (1.20 g, 1.70 eq., 4.4 mL of 27 wt % solution in 2-Me-THF). After seeding with product, the mixture was aged at 60° C. for 20 minutes, another portion of S-mandelic acid (1.22 g, 2.3 eq, 5.95 mL of 27% solution in 2-Me-THF) was charged over 4 hours at 60° C. The temperature was gradually cooled to 20° C. over 8 hour, maintained at 20° C. for 1 hour. The slurry was filtered and the solid was rinsed with 2-Me-THF with 2% wt S-mandelic acid. The wet filter cake was dried at 60° C. to provide Compound A bis-mandelate salt as a solid (4.53 g).

Example 2

Preparation of Compound C

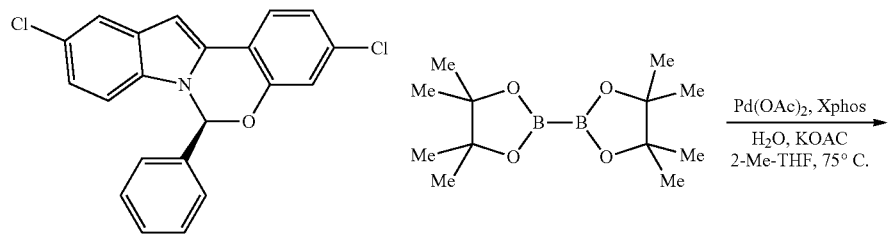

2A

-continued

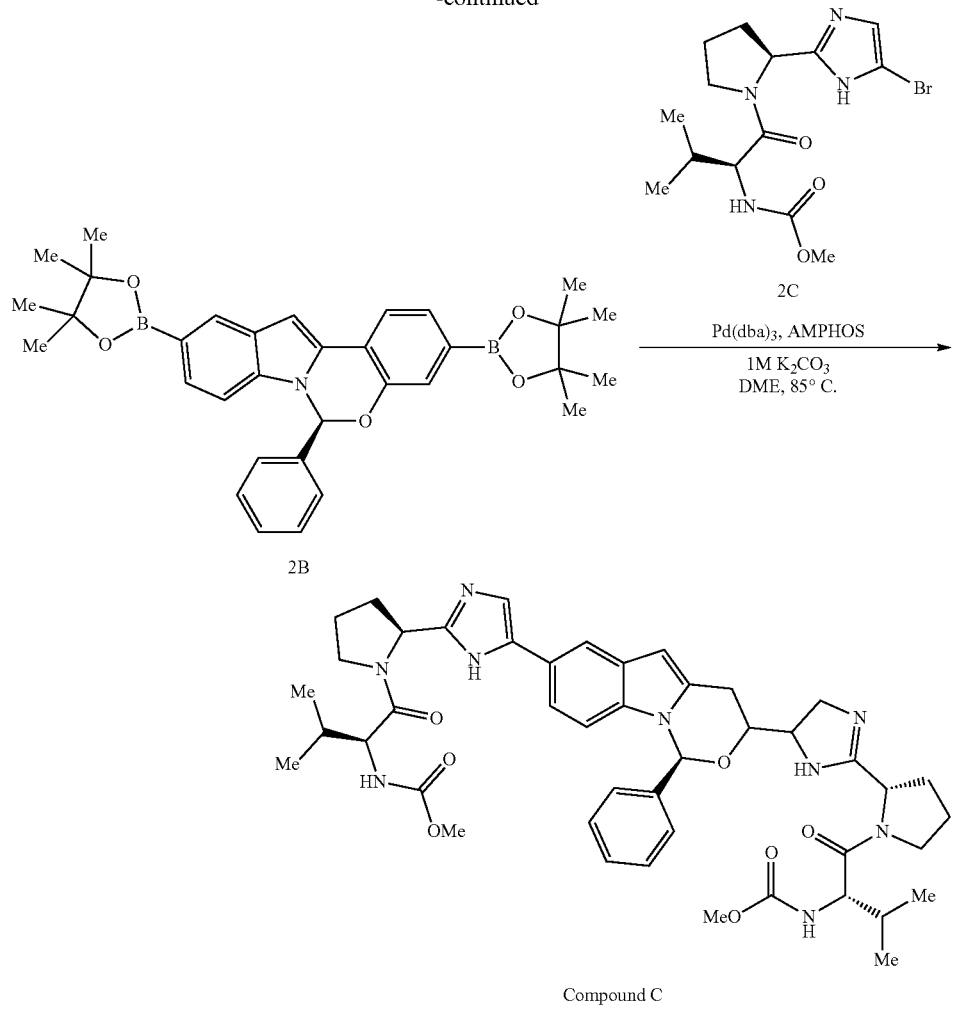

Compound C
40

Step A—Synthesis of Compound 2B

To a 500 mL 3-neck flask, equipped with thermocouple and overhead stirrer was added compound 2A (5 g, 13.65 mmol), 4,4,4',4',5,5,5',5'-octamethyl-2,2'-bi(1,3,2-dioxaborolane) (7.63 g, 30.0 mmol, 2.2 equivalent), KOAc (6.70 g, 68.3 mmol, 5 equivalent) followed by degassed 2-Me-THF (97.5 mL) and degassed water (0.32 mL, 17.75 mmol, 1.3 equivalent). The mixture was purged with nitrogen for an additional 20 minutes. A pre-mixed solution containing $Pd(OAc)_2$ (61 mg, 0.273 mmol, 0.02 equivalent) and XPhos (260 mg, 0.546 mmol, 0.04 equivalent) in 2-Me-THF (2.5 mL) was added to the above solution. The resulting reaction was heated to 75° C. over a period of 10 minutes and the stirring was continued at 75° C. for an additional 2 hours. After being cooled to room temperature, the reaction was diluted with water (50 mL), followed by stirring for 10 minutes. The layers were separated and the organic layer was washed with 10% brine (25 mL), dried over $MgSO_4$, filtered and concentrated in vacuo. The residue obtained was redissolved into 2-Me-THF (50 mL), and $CuNO_3$ (1.25 g) was added. After being stirred at room temperature for 1 hour, the solution was filtered, and the solid was washed with additional 2-Me-THF (25 mL). The organic layer was concentrated in vacuo to provide a residue which was redissolved in 2-Me-THF (40 mL). Then resulting solution was heated to 70° C., then heptane (200 mL) was added dropwise over a period of 15 minutes. After the addition was complete, the mixture was slowly cooled to room temperature over a period of 2 hours, where it was allowed to stir for about 15 hours. The solid was filtered and washed with additional 25 mL of 6:1 heptane:2-Me-THF solution. After drying in vacuo, compound 2B (6.35 g) was isolated as a solid.

Step B—Synthesis of Compound C

To a mixture of compound 2B (200 mg, 0.364 mmol) and compound 2C (285 mg, 0.765 mmol) was added degassed DME (2.1 mL), followed by a degassed solution of $K_2CO_3$ (1.1 mL of 1M solution, 2.185 mmol). The resulting mixture was purged with nitrogen for 15 minutes while stirring. for an additional 15 minutes. A premixed solution of $Pd_2(dba)_3$ (10 mg, 0.010 mmol) and Amphos (5.8 mg, 0.022 mmol) in degassed DME (0.5 mL) was then added to the reaction mixture.

The reaction was heated at 85° C. and allowed to stir at this temperature for 15 hours while maintaining vigorous stirring. After being cooled to room temperature the mixture was diluted with EtOAc (5 mL) followed by water (2 mL). The layers were separated and the organic layer was washed with 10% brine (5 mL), dried over $MgSO_4$, filtered and concentrated in vacuo to provide a residue which was purified using Prep-TLC (2000 micron, eluted with 10:1

DCM:MeOH) to provide compound C as a solid (0.264 g). HPLC and other spectral data matched those of the authentic compound C.
Example 3
Alternate Preparation of Compound A
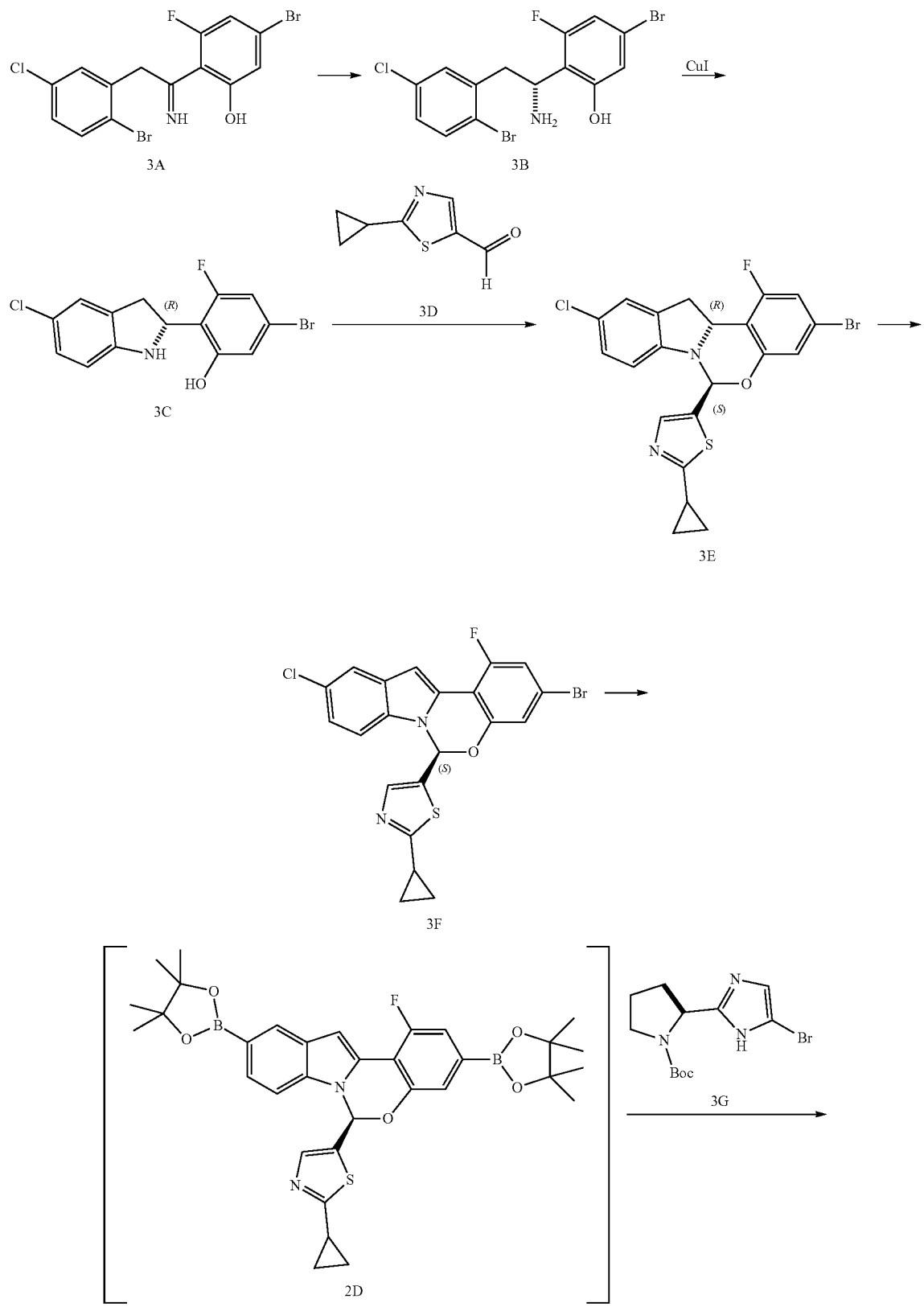

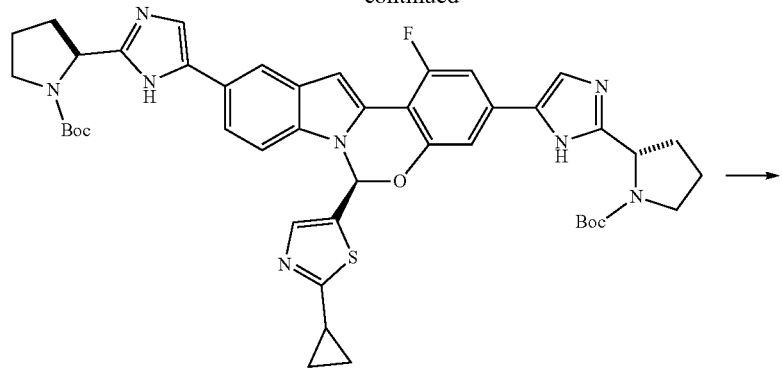

3H

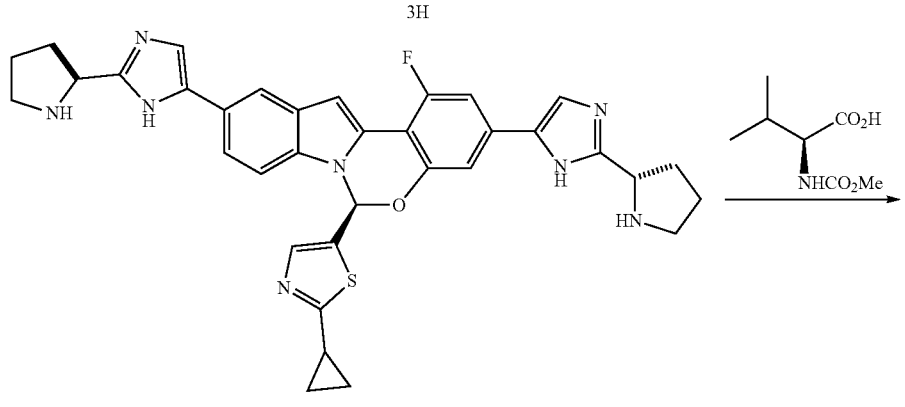

3I

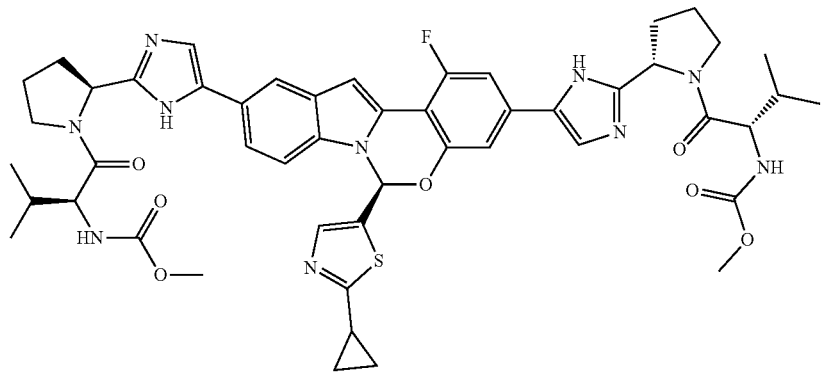

Compound A

Step A—Synthesis of Compound 3B

In a dry 40 mL vial was charged 3A (1.0 g), acetonitrile (10 mL), triethylamine (0.265 mL) and formic acid (0.182 g) under nitrogen. Chloro{N-[(1R,2R)-2-[(S)-[2-[[1,2,3,4,5,6-η)-4-methylphenyl]methoxy]ethyl]amino]-1,2-diphenylethylmethanesulfonamidato}ruthenium(II) (27 mg) was added under nitrogen. The mixture was heated to 70° C. and allowed to stir at this temperature for 2 hours then cooled to room temperature. The mixture was then concentrated in vacuo, and the residue obtained was dissolved in dichloromethane. The mixture was solvent-switched to ethyl acetate, and heptane was added. The solid formed was collected by filtration to provide 3B (0.272 g, 99% ee). The mother liquor was concentrated in vacuo, and the residue obtained was purified using flash column chromatography on silica gel to provide additional 3B (0.548 g, 96% ee).

Step B—Synthesis of Compound 3C

In a 8 mL vial was charged 3B (50 mg, 96% ee), copper(I) iodide (22 mg), cesium carbonate (96 mg) and DMF (0.5 mL) under nitrogen atmosphere. The reaction mixture was heated to 50° C. and allowed to stir at this temperature for 1 hour before cooling to room temperature. The mixture was diluted with ethyl acetate, and quenched with aqueous ammonium chloride. The organic layer was washed with brine, then dried over $Na_2SO_4$, and concentrated in vacuo to provide compound 3C (96% ee). LCMS (M+H) 341.7, 343.7.

Step C—Synthesis of Compound 3E

A solution of compound 3D in MeCN (7.58 kg, 42.5 wt %) was diluted with 14.5 kg of MeCN followed by addition of compound 3C (6.0 kg). The mixture was cooled to 10-15° C. and TFA (0.74 kg) was added, then the mixture was allowed to age at 14-16° C. for 12 hours. Triethylamine (0.78 kg) was then added over 30 minutes at 15-20° C. The reaction mixture was cooled to 0° C. and allowed to age for 2 hours. The mixture was then filtered and the collected solid was washed with 2.75 kg of MeCN, then dried in vacuo to provide compound 3E (7.3 kg, 96.7% HPLC purity and 100% chiral purity). $^1$H NMR (CDCl$_3$, 400 MHz) δ (ppm) 7.50 (d, J=1.2 Hz, 1 H), 7.13-7.09 (m, 2 H), 6.84-6.78 (m, 4 H), 5.07 (d, J=9.6 Hz, 1 H), 3.60-3.53 (m, 1 H), 3.29-3.25 (m, 1 H), 2.26-2.21 (m, 1 H), 1.13-1.11 (m, 1 H), 1.06-1.04 (m, 2 H).

Step D Synthesis of Compound 3F

DMAc (68 kg), compound 3E (7.3 kg), and NaHCO$_3$ (7.7 kg) was charged into a reaction vessel and cooled to 0-10° C. KMnO$_4$ (9.7 kg) was charged followed by dropwise addition of water (14.6 kg) at 0-10° C. The mixture was warmed to 16-20° C. and allowed to age for 16-24 hours, then filtered to remove inorganic salts. The filter cake was washed with ethyl acetate (27 kg×2). The combined filtrates were transferred back to the reaction vessel and treated with 4.4% Na$_2$SO$_3$ in 10% brine (77 kg) at 5-15° C. The temperature was increased to 10-20° C. and allowed to age for 1 hour. The mixture was filtered, and the resulting residue washed with ethyl acetate (27 kg). The aqueous layer of the filtrate was separated and discarded. The organic layer was washed with 10% brine (73 kg×3), concentrated in vacuo and solvent switched to MeOH with a final volume of approximately 90 L. After aging at 13-17° C. for about 4 hours, the product was collected by filtration and washed with 5 L of MeOH. The product was then dried in vacuo at 45-55° C. to provide compound 3F (4.81 kg, 99.9% HPLC purity and 100% chiral purity).

The absolute configuration of 3F was assigned to be (S) using Vibrational Circular Dichroism (VCD) spectroscopy with confidence. Analysis was done comparing experimental data to the calculated VCD and IR spectra of the (S) configuration (see FIG. 1). The experimental VCD spectrum of 3F matched well with the calculated (S) spectrum over the region from 1000-1650 cm$^{-1}$, resulting in an assignment of (S).

Step E—Alternate Synthesis of Compound 3F

To a clean, dry and inerted 1000 L vessel was charged compound 3E (34.9 kg), Mn(OAc)$_2$ 4H$_2$O (1.8 kg) and 1,10-phenanthroline (2.6 kg). The contents were slurried in DMAc (328.1 kg) and MeCN (274.3 kg) and cooled to −10° C., then TBHP (47 kg) was added over a period of approximately 1 hour. The reaction stream was allowed to age at −10° C. for a total of 60 hours, then the reaction stream was warmed to 20° C. and treated with EtOAc (322 kg), and then aged for 1 hour. The contents were then re-cooled to 0° C. for the quench. In a separate 400 L vessel, Na$_2$SO$_3$ (36.8 kg) was dissolved in water (331.2 kg) and the solution was cooled to 0° C. The batch was quenched by adding the Na$_2$SO$_3$ solution to the stream over a period of approximately 1 hour, ensuring T<10° C. during addition. The quenched stream was warmed to 30° C. and allowed to age for 20 minutes. The reaction stream containing indole was washed with 5% LiCl (3×125 L). The organic phase was concentrated in vacuo to a final volume of approximately 40 L, ensuring the batch temperature <40° C. during concentration. Once distillation was complete, MeCN (141 kg) was added and the stream re-concentrated in vacuo to approximately 40 L to remove residual EtOAc. A further charge of MeCN (281.8 kg) was added, and the stream was cooled to 20° C. The solution was seeded with product (240 g) and then allowed to age at 20° C. for about 15 hours. The slurry in MeCN was treated with water (4 vols, 175.7 kg) added in 1 vol portions, over a period 2 hours, then the slurry was allowed to age for about 15 hours. Water was added (0.5 vols) and the mixture was cooled to 0° C. and aged for 1 hour. The product was isolated via filtration, and washed with (MeCN:water 2:1, 3 vols). The damp filter cake was transferred to a vacuum oven and dried in-vacuo at 50° C. for about 15 hours. A total of 23.3 kg of compound 3F was isolated as a solid.

Step F—Synthesis of Compound 2B

To a clean and dry 1000 L vessel was charged compound 3F (10.0 kg @ 90 wt %, and 24.6 kg @ 94 wt %), bis(pinacolato)diboron (37.7 kg), potassium acetate (42.38 kg), XPhos (1.287 kg), and palladium(II) acetate trimer (303 g). The vessel was put under nitrogen atmosphere, and charged with degassed DME (1,2-dimethoxyethane; 333 kg). The resulting stirred mixture was re-inerted (by running a vacuum/nitrogen cycle, followed by sub-surface nitrogen sparging for 20 minutes), heated to 65° C., and then left to age at 65° C. for 4 hrs. The resulting reaction mixture was cooled to 20° C., and then diluted with 2-Me-THF (413 kg). After mixing for 15 minutes, water (96 kg) was added. The resulting biphasic mixture was allowed to stir for 5 minutes, and the two layers were then allowed to settle. The two layers were separated, and the resulting organic layer was washed with aqueous sodium chloride (prepared from 26 kg of NaCl and 86 kg water). The final organic layer was transferred to clean drums, and the 1000 L vessel was rinsed with water and then with DME. The final organic layer was then returned to the rinsed vessel, via a 1 μm in-line cartridge filter, rinsing the addition-line and filter through, into the batch, with 2-Me-THF (15 kg). The resulting solution was then concentrated by distillation under partial vacuum, to a volume of 430 L, while maintaining the batch temperature at <40° C. A slurry of product seed (44 g) in acetonitrile (0.4 kg) was then added, and the resulting mixture was allowed to age at 40° C. for 1 hour, to form a good seed-bed. The batch was then concentrated, by distillation under partial vacuum, to a volume of 195 L, whilst maintaining the batch temperature at <40° C. The resulting slurry was cooled to 20° C. over a period of 2 hours, and then aged at this temperature for 88 hrs. To the resulting stirred slurry was then added acetonitrile (302 kg) over a period of 1 hour. The resulting mixture was allowed to age at 20° C. for 1.5 hours, cooled to 0° C. over a period of 2 hours, and then aged at 0° C. for 21 hours. The resulting slurry was filtered, washing the wet-filter cake with acetonitrile (140 kg). The resulting filter cake was dried on the filter under a stream of nitrogen, at ambient temperature, for 1 hour, and then dried in a tray-dryer in vacuo at 40° C. for about 15 hours to provide compound 2B as a solid (41.79 g, 98 LCAP @ 210 nm; <0.1 A % undesired enantiomer; contained 165 ppm Pd, 60 ppm P, approximately 3800 ppm Na & 19 ppm K).

Step G—Synthesis of Compound 3H

In a 500 mL round bottom flask was charged DME (120 mL) and water (50 mL), and the solution was degassed with nitrogen. Potassium carbonate (13.5 g), compound 2B (10.0 g) and compound 3G (11.32 g) were subsequently added. The mixture was degassed with nitrogen. PdCl$_2$(Amphos)$_2$ (0.288 g) was added, and the mixture was heated at 80° C. and allowed to stir at this temperature for 17 hours before cooling to room temperature. Ethyl acetate (120 g) was added and the aqueous layer was removed. The organic layer was washed with water (60 mL), filtered and concentrated in vacuo to form precipitates out of the solution. The solid was collected by filtration to provide compound 3H (11.2 g). $^1$H NMR (CD3OD, 500 MHz), 7.95 (br s, 1H), 7.81 (br s, 1H), 7.55-7.21 (br m, 6H), 7.12 (br s, 1H), 7.04 (br s, 1H), 3.72-3.64 (br m, 2H), 3.59-3.45 (br m, 2H), 2.45-2.25 (br m, 2H), 2.20-2.15 (m, 1H), 2.15-1.90 (br m, 6H), 1.49 (br s, 6H), 1.25 (br s, 6H), 1.24 (br s, 6H), 1.08-1.01 (m, 4H), 0.91-0.85 (m, 4H).

Step H—Synthesis of Compound 31

To compound 3H (11.16 g, 13.40 mmol) in MeOH (190 mL) and MeCN (95 mL) was charged HCl (11 mL, 37%). The reaction was allowed to age at room temperature for 10 minutes and then warmed to 46° C. and allowed to stir at this temperature for about 15 hours. The slurry was gradually cooled to room temperature, aged at this temperature for 2 hours and filtered. The wet filter cake was washed with MeOH/MeCN (1:2, 60 mL) and dried in vacuo at 60° C. to provide compound 3I as its quaternary HCl salt (8.15 g).

Step I—Synthesis of Compound A

To the HCl salt of compound 3I (3.3 g, 4.24 mmol) was charged MeCN (40 mL) and (S)-2-((methoxycarbonyl) amino)-3-methylbutanoic acid (1.783 g, 10.18 mmol). The slurry was cooled to 5° C. followed by addition of 4-methylmorpholine (3.26 mL, 29.7 mmol). The reaction was allowed to age for 5 minutes until dissolution, then HOBt (0.325 g, 2.121 mmol) was added, followed by EDC.HCl (1.95 g). The reaction was aged at 0° C. for 3 minutes, then at room temperature for about 15 hours and worked up with water (15 mL)/EtOAc (40 mL). The organic layer was washed with NH₄Cl (15 mL, 2 M), 10% NaHCO₃ (2×15 mL), and water (15 mL), then filtered and concentrated in vacuo to provide compound A (3.59 g, 70%).

Example 4

Alternate Preparation of Compound 3C

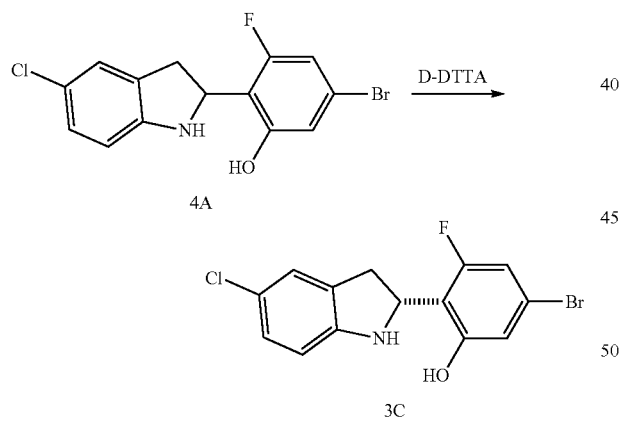

A solution of D-DTTA (45 kg) was prepared by dissolution in MeOH (164 kg). Compound 4A (racemic, 40 kg) was dissolved in MeOH (475 kg) by heating to 55-70° C. The D-DTTA solution (204 kg) was added to the Compound 4A solution over 3 hours and the resulting mixture was cooled to 40-45° C.—noting that a seed bed started to form. The mixture was cooled to 3-8° C. and allowed to age at this temperature for about 18 hours. The product was collected by filtration and washed with MeOH (73 kg×2). The wet filter cake was transferred back to a vessel containing MTBE (426 kg) and water (148 kg). After aging at 15-25° C. for 1 hour, 1N NaOH (114 kg) was added at 15-25° C. until the solution was at pH 8-9. The layers were separated and the aqueous layer was back extracted with MTBE (113 kg). The combined organic layers were washed with water (140 kg×2) and 25% brine (160 kg). The organic layer was then concentrated in vacuo and solvent switched to EtOH to a volume of 200-240 L. Water (44 kg) was added at 15-25° C. when a seed bed started to form. More water (320 kg) was added over 3 hours and the mixture was allowed to age for about 6 hrs. The product was collected by filtration and washed with 1.1/1 EtOH/water (51 kg). Drying at 45-50° C. in vacuo provided compound 3C (17.05 kg, 99.5% HPLC purity and 100% chiral purity). Chiral chromatographic conditions: CHIRALCEL OD-RH (150×4.6 mm, 5 µm), 210 nm, 40° C., 0.8 mL/min, mobile phase A: 0.1%H₃PO₄ in H₂O, B: ACN, gradients: 0 minutes: 90% A, 5 minutes: 35% A, 20 minutes, 10% A. Desired enantiomer RT: 18.4 minutes, undesired enantiomer RT: 16.3 min.

Example 5

Alternate Preparation of Compound 3F via Chiral Separation

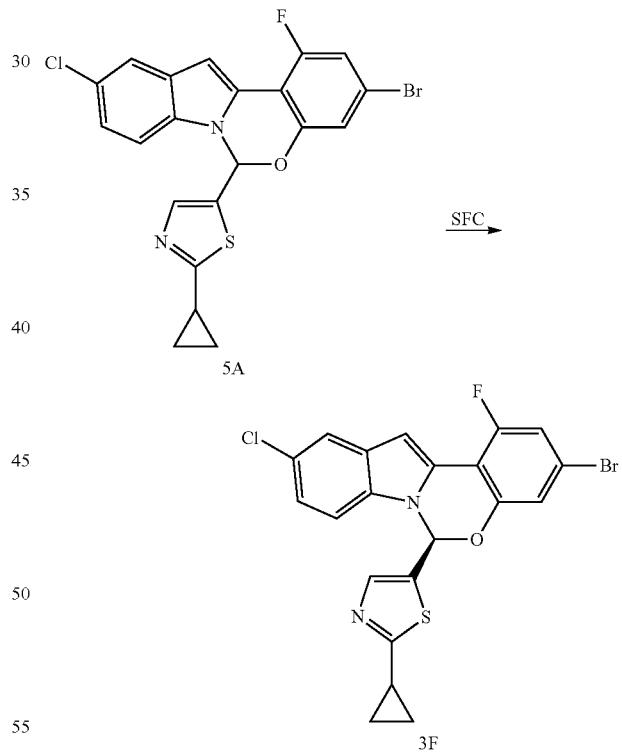

Racemic compound 5A (65 g) was separated using SFC using the following conditions to provide compound 3F (30 g, 46% yield). Instrument: Thar SFC; Column: Chiralpak AS-H 150×4.6 mm I.D., 5 µm; Mobile phase: A for CO₂ and B for EtOH (0.05%DEA); Gradient: B. 5% to 40 for A in 6.4 min; Flow rate: 2.5 mL/min; Back pressure: 100 bar; Column temperature: 35° C.; Wavelength: 220 nm. Desired enantiomer RT: 4.4 minutes, undesired enantiomer RT: 4.8 minutes.

Example 6

Alternate Preparation of Compound 2B via Chiral Separation

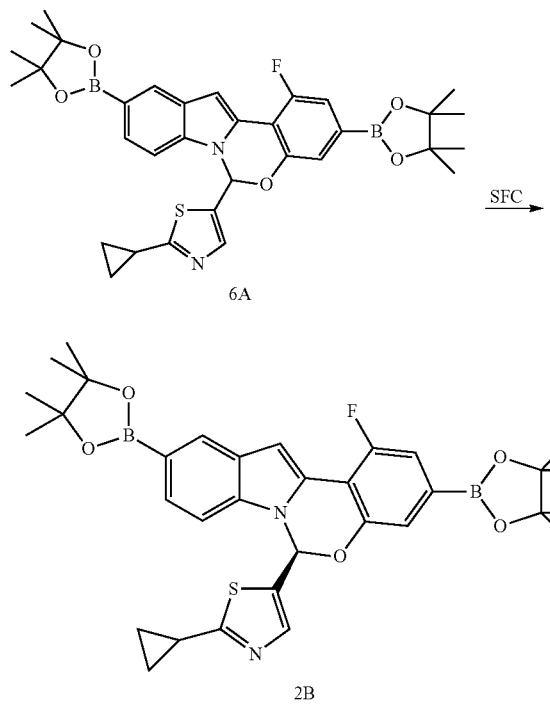

Racemic compound 6A was separated using SFC under the following conditions to provide compound 2B. Instrument: Thar SFC; Chiralpak IC (250×4.6 mm, 5 μm), 240 nm, 20° C., 0.8 mL/min, mobile phase A: water, B: ACN: isopropanol=8:2(V/V), isocratic A:B=30:70. 32 minute run time. Desired enantiomer RT: 19.3 minutes, undesired enantiomer RT: 21.5 minutes.

Example 7

Preparation of Compound 1C

Step A—Synthesis of Compound 7B

To a solution of compound 7A (1, 15 g, 91 wt %, 57.5 mmol) in 150 mL of ethyl acetate was added 0.75 mL of water, 9.7 g of NaHCO$_3$ (1.8 eq.) and 17.7 g N-chlorosuccinimide (2.3 eq.) at 5° C. The mixture was allowed to stir 5° C. for 30 minutes and warmed up to 20° C. The reaction was allowed to stir at 20° C. for 5 hours. 135 mL of water was added and the organic layer was separated. The aqueous layer was extracted with 30 mL of ethyl acetate. The combined organic layers were mixed with 150 mL of 5% sodium metabisulfite solution. The mixture was allowed to stir at room temperature for 30 minutes, then the aqueous layer was removed and the organic layer was washed with 45 mL of water. The solution was then concentrated in vacuo and the residue obtained was dissolved in 150 mL of acetonitrile. The solution was treated with 6 g of Darco G-60 for 2 hours at room temperature. The mixture was filtered and the filtrate concentrated in vacuo to 75 mL in vacuo. The solution was cooled to 5° C. and 210 mL of water was added slowly over 2 hours. The resulting suspension was filtered and the filter cake was washed with 30% solution of acetonitrile in water. The solid was dried in the oven to provide compound 7B (12.3 g) as a solid. $^1$H NMR for a mixture of two rotamers (approximately 6:4 ratio: NMR reported as 6:4 mixture) (500 MHz, DMSO-d$_6$) δ 13.02 (br s, 1 H), 4.67 (br s, 0.4 H), 4.59 (br s, 0.6 H), 3.50 (m, 1 H), 3.32 (m, 1 H), 2.30-2.10 (m, 1 H), 1.95-1.77 (m, 3 H), 1.38 (s, 3.6 H), 1.18 (s, 5.4 H). $^{13}$C NMR for the major rotamer (100 MHz, DMSO-d$_6$) δ 154.1, 148.9, 123.3, 108.9, 79.0, 55.7, 46.7, 33.5, 28.3, 23.4. $^{13}$C NMR for the minor rotamer (100 MHz, DMSO-d$_6$) δ 153.5, 148.4, 123.2, 108.9, 79.1, 55.2, 46.9, 32.3, 28.6, 24.4.

Step B—Synthesis of Compound 7C

A mixture of 127 mg (0.03 eq.) of PdCl$_2$(MeCN)$_2$ and 260 mg (0.06 eq.) of 4-(N,N-dimethylamino)phenyldi-tert-butylphosphine in 15 mL of deoxygenated toluene was heated at 50° C. for 2 hours under nitrogen to provide a suspension. In another flask, 5.0 g of compound 7B, 3.4 mL (1.3 eq.) of triethylsilane, 4.3 mL (1.5 eq.) of diisopropylethylamine and 90 mL of toluene were mixed under nitrogen. The mixture was heated to 40° C. and the resulting solution was transferred into the catalyst suspension via cannula under nitrogen. The resulting mixture was heated at 110° C. for about 6 hours until HPLC analysis indicated the conversion reached about 95% containing about 90% compound 7C, 5% of compound 7A and 5% of compound 7B. The solution was then cooled to room temperature and treated with 40 mL of 1M phosphate buffer solution at pH 3.5. The aqueous

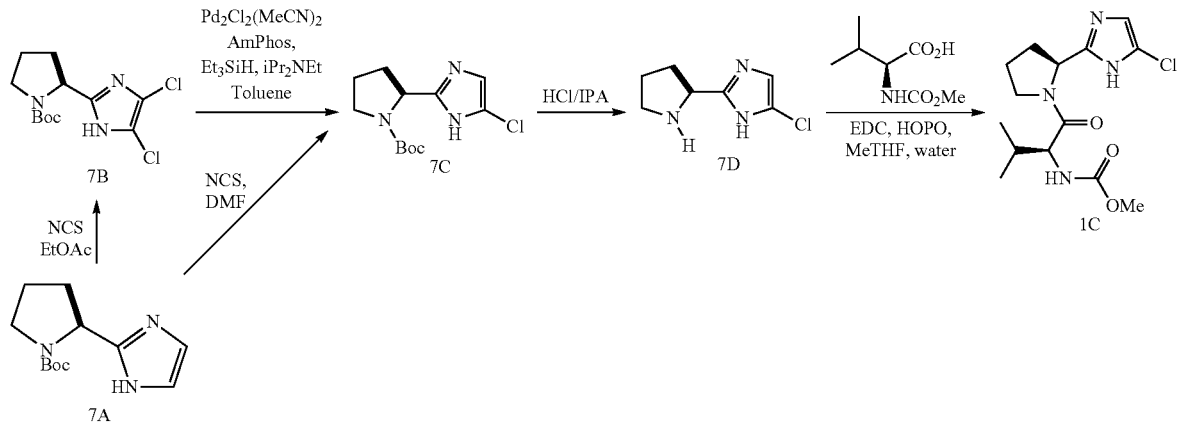

phase was discarded. The organic phase was mixed with 40 mL of 1M $H_3PO_4$ solution at 5° C. The mixture was allowed to stir at 5° C. for 10 minutes and the aqueous was separated. The organic layer was extracted two more times with another 20 mL of 1M $H_3PO_4$ solution, and the combined organic extracts were discarded and the combined aqueous layers were mixed with 50 mL of toluene. NaOH solution (25%) was added dropwise at 5° C. until the solution was basic. The organic layer was separated and washed with 20 mL of water. The resulting solution was concentrated in vacuo to about 15 mL, then heptane (60 mL) was added slowly over 2 hours at room temperature, and the resulting suspension was cooled to below 5° C. The solid was collected by filtration followed by drying in a vacuum oven to provide compound 7C as a solid (3.0 g). $^1$H NMR for a mixture of two rotamers (approximately 6:4 ratio: NMR reported as 6:4 mixture) (400 MHz, DMSO-$d_6$) δ 12.10 (br s, 0.6 H), 12.05 (br s, 0.4 H), 7.05 (br s, 0.6 H), 7.00 (br s, 0.4 H), 4.70 (br s, 0.4 H), 4.65 (br s, 0.6 H), 3.49 (br, 1 H), 3.30 (m, 1 H), 2.30-2.10 (m, 1 H), 2.00-1.70 (m, 3 H), 1.38 (s, 3.6 H), 1.18 (s, 5.4 H). $^{13}$C NMR for the major rotamer (100 MHz, DMSO-$d_6$) δ 153.7, 149.6, 126.9, 111.6, 78.7, 55.5, 46.7, 33.6, 28.3, 23.4. $^{13}$C NMR for the minor rotamer (100 MHz, DMSO-$d_6$) δ 154.2, 148.9, 126.9, 112.2, 79.1, 54.9, 46.9, 32.1, 28.6, 24.2. MP 144-146° C. Calcd. exact mass for $C_{12}H_{18}ClN_3O_2$ [M+H]$^+$: 272.1166; found: 272.1182

Step C—Alternate Synthesis of Compound 7C

A mixture of 7A (20.00 g), isopropyl acetate (300 mL) and water (100 mL) was agitated for 30 minutes at 25° C. N-Methylmorpholine (0.47 mL) was added, and the mixture was cooled to 5° C. DCDMH (8.47 g) was then added and the mixture was aged at 5° C. for 18 hours. $Na_2S_2O_5$ was then added as a solid in two portions (in total 5.34 g), and the mixture stirred for about 1 hour at 5° C. The pH of the aqueous phase was adjusted to 3.3 using 1M $H_3PO_4$ (7.5 g). The organic layer was extracted with 1M $H_3PO_4$ three times (200 mL, 100 mL, then 100 mL) while maintaining batch temperature below 8° C. The three aqueous extraction layers were combined, and isopropyl acetate (200 mL) was added. The pH was adjusted to 6 with 50% wt NaOH (approximately 38.9 g) while maintaining the batch temperature around 5° C. The organic layer was then concentrated, flushed with isopropyl acetate, filtered (at 55° C.) to remove inorganics. The batch was further concentrated in vacuo to 35 mL and heptane (100 mL) was added at 55° C. The batch was then concentrated in vacuo to 65 mL and cooled to 20° C. over 2 hrs. The product was collected by filtration and washing with 9:1 vol/vol n-Heptane-isopropyl acetate (2×20 mL). Drying in a vacuum oven at 40° C. provided compound 7C (12.82 g).

Step D—Alternate Synthesis of Compound 7C

To a solution of 10.0 g (95%, 40 mmol) of compound 7A in 100 mL of N,N-dimethylacetamide was added 1.5 g (0.44 eq) of $NaHCO_3$ and 6.0 g (1.12 eq.) of N-chlorosuccinimide at –10° C. The mixture was allowed to stir at –10° C. for 3 hours and warmed up to –5° C. After the mixture was allowed to stir at –5° C. for 3 hours, the reaction was quenched by addition of 80 mL 5% sodium metabisulfite. The mixture was allowed to stir for 30 minutes at 15° C. and 100 mL of toluene was added. The mixture was heated to 40° C., and the organic layer was separated. The aqueous layer was extracted with 40 mL of toluene. The combined organic layers were then treated with 70 mL of 1M phosphate buffer (pH 3.50) at room temperature, then the resulting solution was cooled to 5° C., and 80 mL of 1M $H_3PO_4$ solution was added. The resulting mixture was allowed to stir for 5 minutes, and the aqueous layer was separated. The organic layer was extracted with 5° C. 1M $H_3PO_4$ (2×40 mL). The product was extracted into toluene followed by crystallization in a mixture of toluene and heptane similarly as described above, to provide compound 7C (5.0 g).

Step E—Synthesis of Compound 7D

To a solution of compound 7C (10 g) and 30 mL isopropanol at 60° C. was added 5.4M HCl in isopropanol (26.4 mL) over 1.5 hours. After aging for another 1 hour, the slurry was cooled to 10-15° C. and filtered with 40 mL isopropanol wash. The collected solid was dried in vacuo to provide 7D (8.55 g).

Step F—Synthesis of Compound 1C

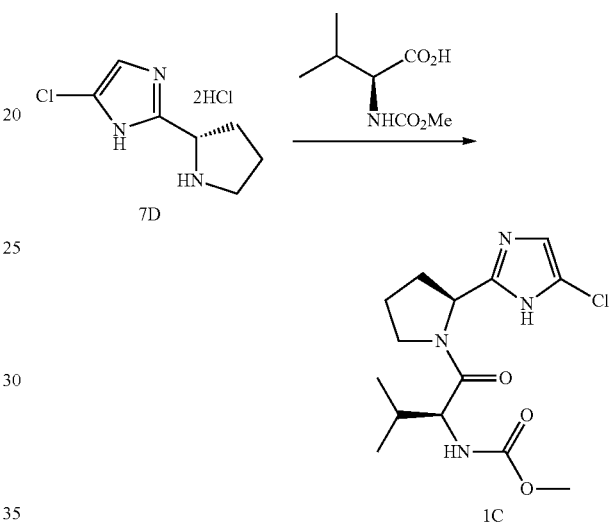

A mixture of compound 7D (10 g, 40.6 mmol), Mocvaline (7.47 g, 42.6 mol), and 2-Me-THF (150 mL) to vessel was cooled to about –5° C. Water (20 mL) was added and the slurry turned into biphasic solution. 10 wt % NaOH (29.2 g, 73.1 mmol) was charged into the vessel with good agitation over 30 minutes. The pH of the mixture at this point was approximately 5.6. The batch temperature was adjusted to about 23° C., then 1M $NaHCO_3$ (8.12 mL, 8.12 mmol, alternatively 2.5 wt. % NaOH solution can be used in place of 1M $NaHCO_3$) was added to the vessel slowly, resulting in the solution adjusting to pH 6.5. HOPO (0.45 g, 4.06 mmol) was added and the mixture was allowed to age for 10 minutes at about 23° C. EDC.HCl (9.34 g, 48.7 mmol) was charged, and the batch was aged at about 23° C. for 15 hours. The organic layer was treated with 5% $NaHCO_3$ (50 mL) at 40-50° C. for 1-2 hours. The organic layer was then washed with 5% $NaHCO_3$ (50 mL), then brine (2×30 mL). The combined aqueous layers were back extracted with 2-Me-THF (50 mL). The organic layer was washed with water (20 mL), then the combined organic layers were concentrated in vacuo to approximately 50 mL at 30-40° C. until KF reached <1500 ppm water. The mixture was cooled to 25-30° C. and seeded. After aging the slurry for 1 hour, n-heptane (100 mL) was added over 10 hours at 25-30° C. After aging the slurry again for 2 hours at 25-30° C., it was cooled down to 15-20° C. over 2 hours. After additional aging for 2 hours at 15-20° C., the slurry was filtered and washed with 1:2 2-Me-THF/heptane (30 mL) and then heptane (30 mL). Drying in vacuo provided compound 1C (12 g).

Example 8

Preparation of Compound 3D

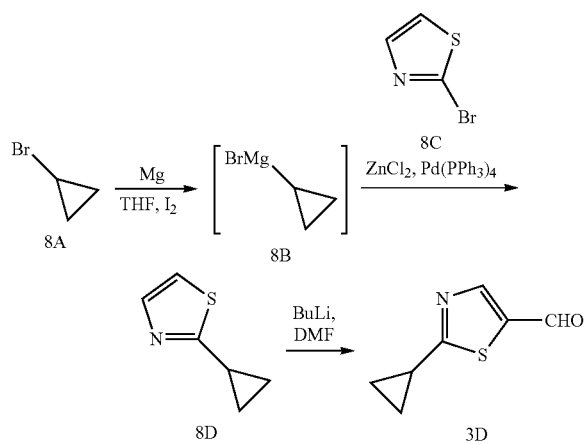

Step A—Synthesis of Compound 8D

In a first reaction vessel, THF (120 mL), magnesium (7.3 g) and cyclopropylmagnesium bromide THF solution (5.6 g) were charged. The mixture was degassed with argon, then heated to 40-50° C. Compound 8A (3.7 g) was added over 10 minutes at 40-50° C. The mixture was allowed to age at 40-50° C. for 30 minutes, then a solution of additional compound 8A (33.2 g) in THF (250 g) was added over 2 hours at 40-50° C. The mixture was sitrred at 40-50° C. for about 20 hours then cooled to 30-35° C. To a second reaction vessel was charged 2-Me-THF (43 g) and zinc chloride (12.8 g). The mixture was filtered to remove precipitates, and transferred to the third reaction vessel. Compound 8C (25 g) and THF (110 g) were then added to the third reaction vessel. The mixture in third reaction vessel was degassed with argon. Pd(PPh$_3$)$_4$ (3.6 g) was added to the third reaction vessel at 20-30° C., then the solution in the first reaction vessel (395 mL) was added to the third reaction vessel over 2 hours at 20-30° C. The resulting reaction was allowed to stir for about 24 hours at 10-20° C., then the reaction mixture was filtered through a Celite pad, and the wet filter cake was rinsed with THF (100 g). The filtrate was washed with 150 g of 1 N NaOH in 10% brine three times. The combined aqueous layer was back-extracted with MTBE (95 g). The combined organic layer was washed with 25% brine (150 g) three times. The organic layer was transferred into the third reaction vessel, and 1 N HCl (150 g) was added at 20-30° C. The mixture in the third reaction vessel was concentrated in vacuo at below 30° C. jacket temperature to remove most of THF and MTBE. The resultant aqueous layer was washed with dichloromethane (35 g) three times. The combined organic layer was back-extracted with 1 N HCl (50 g), and the combined aqueous layer was washed with dichloromethane (35 g). The aqueous layer was adjusted to pH 8~9 using 1 N NaOH (320 g), then the aqeuous layer was extracted with MTBE (90 g) twice. The combined organic layers were washed with 25% brine (50 g), then concentrated in vacuo to provide compound 8B.

Step B—Synthesis of Compound 3D

In a reaction vessel (R1) was charged THF (225 mL) and crude 8B (45.6 g). The mixture was degassed with nitrogen, and cooled to −70 to −60° C. n-Butyllithium (175 mL) was added to R1 at −70 to −60° C. Diisopropylamine (9.23 g) was added to R1 at −70 to −60° C. Dimethylformaide (47.88 g) was added to R1 at −70 to −60 C over 2 hours before aging for an additional 1 hour at −70 to −60° C. Acetic acid (141.57 g) in THF (146 mL) was added to R1 at −70 to −60° C. over 2 hours. Water (436 mL) was added to R1, then isopropyl acetate (436 mL) was added. Layers were separated, and the aqueous layer was back-extracted with isopropyl acetate (45.6 mL). The combined organic layer was washed with 5% LiCl solution (228 mL), then brine (684 mL) three times. The organic layer was concentrated in vacuo below 45° C., and solvent-switched to EtOH (1.5~1.7 volume). The mixture was seeded with seed crystals of 3D at 20-25° C., and allowed to stir for 1 hour. Water (200 mL) was added at 20-25° C. for 2 hours. The mixture was cooled to −5~0° C., and allowed to stir for 3~4 hours before filtration to provide 3D (11.5 g). $^1$H NMR (DMSO-d$_6$, 500 MHz) 9.93 (s, 1H), 8.47 (s, 1H), 2.57-2.51 (m, 1H), 1.26-1.22 (m, 4H), 1.12-1.09 (m, 4H).

Example 9

Alternative Preparation of Compound 8D

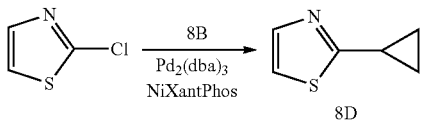 [SMILES: Clc1nccs1 ; c1csc(C2CC2)n1]

To degassed THF (60.0 mL) at room temperature was charged 4,6-bis(diphenylphosphino) phenoxazine (0.111 g, 1.004 mmol) and Pd$_2$(DBA)$_3$ (0.092 g, 0.100 mmol), followed by 2-chlorothiazole (3 g, 25.09 mmol). The mixture was degassed with argon at 15-25° C. It was then heated to 50-60° C. followed by addition of 67 mL compound 8B (0.58 M in THF, 39 mmol) over 1 hour at 50-60° C. The reaction was allowed to age for 1 hour at 50-60° C. then was worked-up and isolated as described above in Example 8, Step A, to provide compound 8D.

Example 10

Preparation of Compounds 3D and 10C

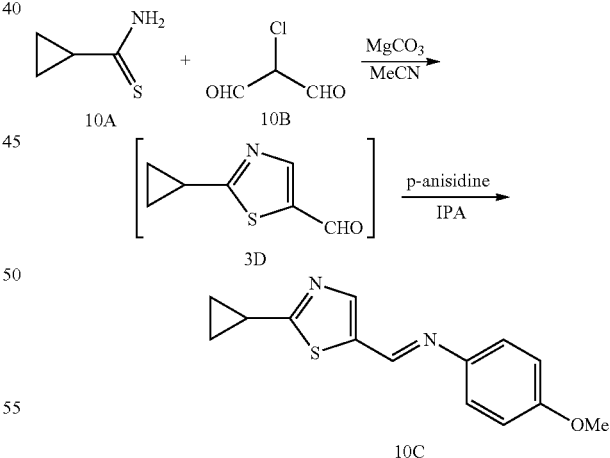

Step A—Synthesis of Compound 3D

In a 250 mL round-bottomed flask with an overhead stirrer was charged 10A (10.0 g), 10B (11.58 g), magnesium carbonate (8.33 g) and acetonitrile (100 mL) under nitrogen. The mixture was heated at 50-55° C. for 10 hours before cooling to room temperature. The mixture was filtered through a Celite pad. The filtrate was concentrated in vacuo to a volume of approximately 25 mL. Toluene (150 mL) and Celite (5 g) were added, and the mixture was washed with 1 M sodium carbonate solution (100 mL). The mixture was again filtered through a Celite pad. The layers were separated, and the organic layer was washed with water (70 mL). The organic layer was separated, and concentrated in vacuo, and solvent-switched to isopropanol (total volume approximatelyl 100 mL). The solution, which contained compound 3D, was stored in a 250 mL round-bottomed flask.

Step B—Synthesis of Compound 10C

To the solution of compound 3D (as prepared in Step A immediately above) was added p-anisidine (12.71 g). The mixture was heated to 80° C., and after 30 minutes, seed crystals were added to initiate crystallization. The mixture was continued to be heated at 80° C. for total of 3 hours before cooling to 4° C. The resultant slurry was filtered to collect the solid. The wet solid was washed with cold isopropanol (50 mL×2), then dried under a nitrogen stream to provide 10C (20.7 g). $^1$H NMR (DMSO-$d_6$, 500 MHz), 8.77 (s, 1H), 8.06 (s, 1H), 7.27 (d, J=8.6 Hz, 2H), 6.94 (d, J=8.7 Hz, 2H), 3.78 (s, 3H), 2.49-2.43 (m, 1H), 1.22-1.18 (m, 4H), 1.07-1.04 (m, 4H).

Example 11

Alternate Preparation of Compound B

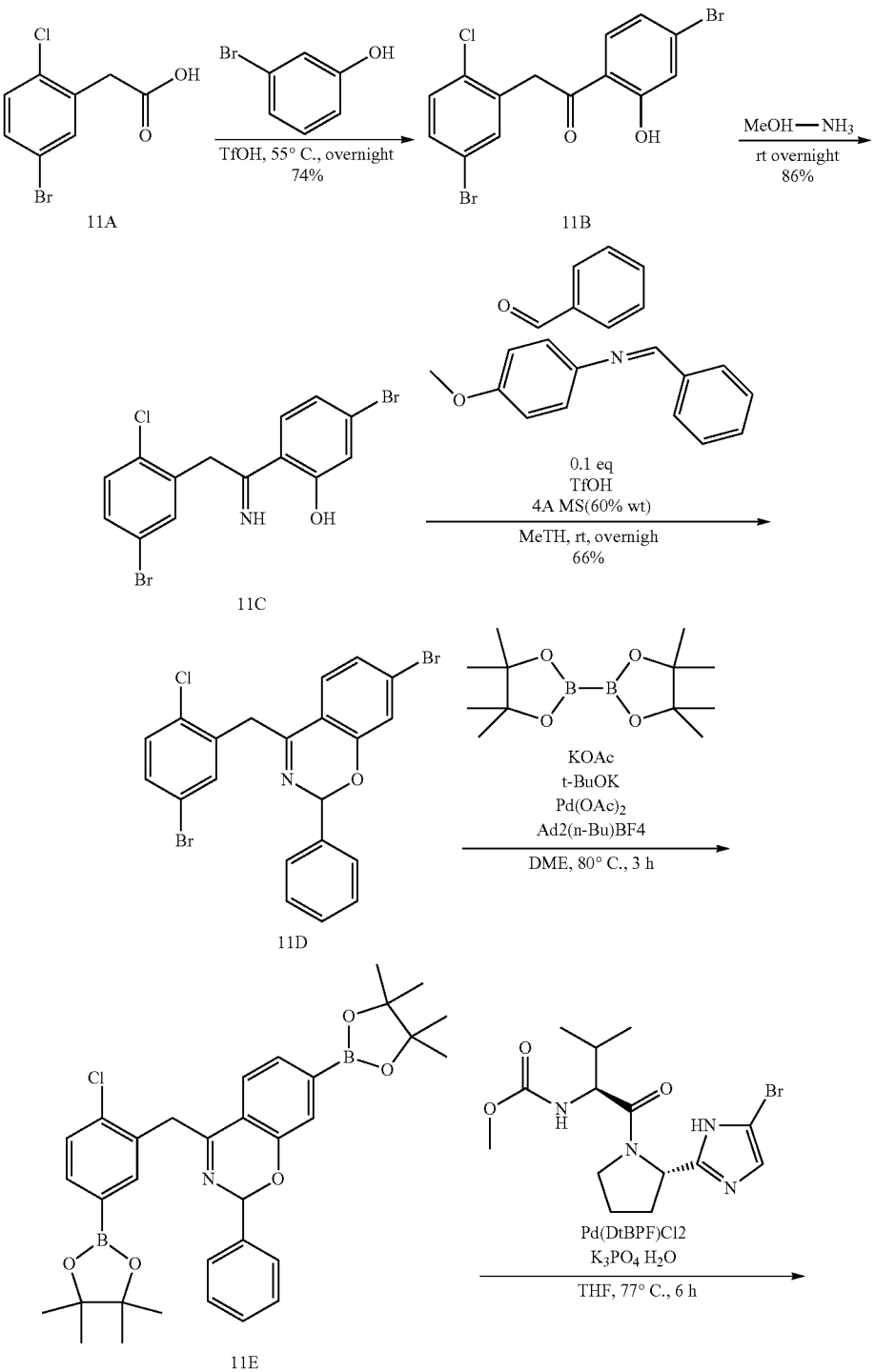

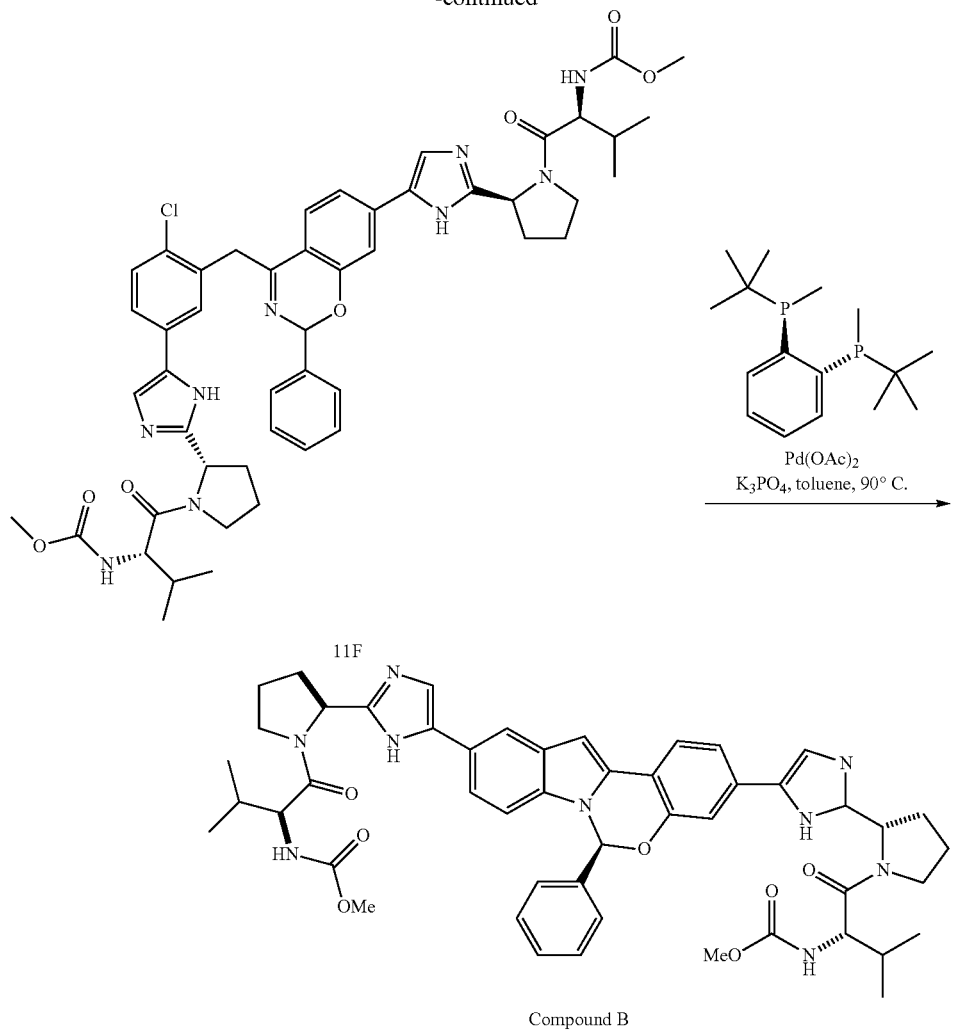

Compound B

Step A—Synthesis of Compound 11B

Trifluoromethanesulfonic acid (526 g, 3507 mmol) was added to 2-(5-bromo-2-chlorophenyl)acetic acid (11A, 35 g, 140 mmol) and 3-bromophenol (21.84 g, 126 mmol). The resulting solution was heated to 55° C. and allowed to stir at this temperature for about 15 hours. After cooling to room temperature, the mixture was diluted with water (1000 mL), then extracted with EtOAc (500 mL×2). The combined organic layers were washed with water (500 mL×2) and brine (200 mL), dried over $Na_2SO_4$, filtered and concentrated in vacuo to provide 11B (42 g, 104 mmol, 74.0% yield) as a solid.

Step B—Synthesis of Compound 11C

A solution of ammonia (400M, 7 M in MeOH) was added to 11B (42 g, 104 mmol) and the mixture was allowed to stir at room temperature for 20 hours. The slurry was filtered, and the product filter cake was washed with MeOH (100 mL×2). After vacuum drying, compound 11C (36 g, 89 mmol, 86% yield) was obtained as a solid.

Step C—Synthesis of Compound 11D

To a 500 mL flask was charged 4A MS (18 g) and Me-THF (252 mL). The solution was allowed to stir for 2 hours at 20° C. Compound 11C (36 g, 89 mmol) and N-benzylidene-4-methoxyaniline (1.885 g, 8.92 mmol) and benzaldehyde (10.42 g, 98 mmol) was added at room temperature. After 10 minutes, trifluoromethanesulfonic acid (2.68 g, 17.84 mmol) was added. The mixture was allowed to stir at room temperature for 15 hours. LCMS showed complete conversion. 5% $NaHCO_3$ (500 mL) was added, and the mixture stirred for other 30 min. Organic layer was separated, and the aqueous layer was re-extracted with EA (200 mL×1). The combined organic layers were dried with $Na_2SO_4$, filtered and concentrated in vacuo. The crude was purified using flash column chromatography on silica gel (A: water (0.05% $NH_4HCO_3$), B: ACN, 85%-100%, 15min) to provide compound 11D (29 g) as an oil.

Step D—Synthesis of Compound 11E

To a 1-L round bottomed flask equipped with an overhead stirrer and a nitrogen inlet was charged DME (290 mL), which was degassed with nitrogen. Compound 11D (29 g, 59.0 mmol), 4,4,4',4',5,5,5',5'-octamethyl-2,2'-bi(1,3,2-dioxaborolane) (33.0 g, 130 mmol) and potassium acetate (34.7 g, 354 mmol) was charged to the flask as solids, and the flask was further purged with nitrogen.

To a 3-neck 500 ml round bottomed flask equipped with an overhead stirrer and a nitrogen inlet was charged DME (290 mL) which was then degassed with nitrogen. $Ad_2$(n-Bu)P $HBF_4$ (1.273 g, 3.54 mmol), t-BuOK (0.397 g, 3.54 mmol) and palladium acetate (0.397 g, 1.770 mmol) were then charged and the mixture aged under nitrogen for 30 minutes to provide a catalyst solution. The catalyst solution was transferred to the solution of compound 11D under nitrogen, and the reaction mixture was heated to reflux (80-83° C.) and allowed to age at this temperature for 4 hours. The reaction was cooled to room temperature, then filtered. The filtrate was concentrated in vacuo to provide compound 11E as a syrup, which was used without further purification.

Step E—Synthesis of Compound 11F

To a 50 mL round bottomed flask equipped with an overhead stirrer and a nitrogen inlet was charged THF (20 ml), which was degassed with nitrogen. Compound 11E (942 mg, 1.608 mmol), $K_3PO_4$ (569 mg, 2.68 mmol), water (5 ml) and 1,1'-Bis (di-tert-butylphosphino)ferrocene palladium dichloride (61.1 mg, 0.094 mmol) was charged to the flask, and the flask was further purged with nitrogen. The reaction was heated to reflux (77° C.) and allowed to age at this temperature for 5 hours. The reaction mixture was cooled to room temperature, and the reaction mixture was directly purified using flash column chromatography on silica gel, then lyophilized to provide compound 11F (122 mg). LC-MS: (ES, m/z): 918 [M+H]+. $^1$H-NMR: 1H NMR (400 MHz, Methanol-d4) δ 7.66 (s, 1H), 7.55 (s, 3H), 7.47 (s, 1H), 7.43-7.32 (m, 5H), 7.16 (s, 1H), 6.48 (s, 1H), 5.11 (q, J=7.2, 5.9 Hz, 1H), 4.25-4.14 (m, 2H), 3.96 (s, 2H), 3.83 (s, 2H), 3.63 (d, J=1.8 Hz, 4H), 3.34 (s, 1H), 2.34-2.23 (m, 3H), 2.14 (s, 2H), 2.01 (tt, J=15.9, 8.1 Hz, 4H), 0.99-0.80 (m, 11H).

Step F—Synthesis of Compound B

Compound 11F (161 mg, 0.175 mmol) and 3 mL toluene was charged to a vial. The catalyst solution was prepared by dissolving 19.6 mg $Pd(OAc)_2$ in 5 mL toluene followed by addition of 24.7 mg (R,R)-(+)-1,2-bis(t-butylmethylphosphino)benzene. After aging at room temperature for 30 minutes, 0.50 mL of the catalyst solution (0.0088 mmol, 0.050 equiv) was added to the above starting material solution in toluene followed by 205 mg of $K_3PO_4$ (0.96 mmol, 5.5 equiv). The mixture was heated at 90° C. for 25 hours when it reached complete conversion to compound B. The d.e. was determined to be 92%. Chiral method used is: Regiscell 250×4.6 mm, 5 μm, MeOH with 25 mM isobutanol, 35% modifier/65% $CO_2$, 3.0 mL/min, 200 bar, 35° C., desired product: 10.0 min, undesired diastereomer: 8.2 min.

Example 12

Preparation of Catalyst 12A

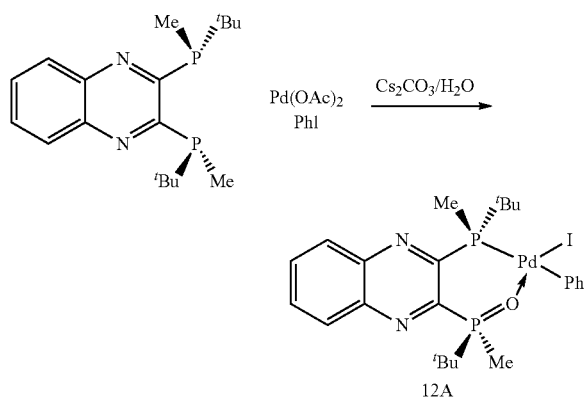

In a glovebox, a solution of palladium(II)acetate (0.134 g, 0.598 mmol), (R) QUINOX-P(R) (0.2 g, 0.598 mmol), and iodobenzene (0.305 g, 1.495 mmol) in 10 mL degassed toluene was allowed to stir for 1 hour at room temperature. $Cs_2CO_3$ (0.974 g, 2.99 mmol), then water (0.054 g, 2.99 mmol) were then added to the reaction over 30 seconds. The reaction was allowed to stir at room temperature for an additional 15 hours, then the reaction mixture was filtered and concentrated in vacuo. The residue obtained was purified using flash column chromatography on silica gel (ethyl acetate/Hex: 2/1) to provide 12A as a solid (0.32 g). $^1$H NMR (500 MHz, CDCl$_3$): δ (ppm) 8.22-8.16 (m, 2H), 8.00-7.95 (m, 2H), 7.39 (1H, dd, J=7.5, 1.0 Hz), 7.14 (1H, dt, J=7.5, 1.5 Hz), 6.94 (1H, t, J=7.5 Hz), 6.90 ((1H, dd, J=7.5 Hz), 6.77 (1H, t, J=7.5 Hz), 2.00 (3H, d, J=13.0 Hz), 1.61 (9H, d, J=16.0 Hz), 1.27 (9H, d, J=16.0 Hz), 1.17 (3H, d, J=13.0 Hz). $^{13}$C NMR (125 MHz, CDCl$_3$) δ (ppm) 154.2 (dd, J=103.1, 23.2 Hz), 152.9 (dd, J=28.3, 18.4 Hz), 141.3 (dd, J=7.0, 2.4 Hz), 140.2, 140.0 (d, J=15.9 Hz), 138.0 (d, J=3.1 Hz), 136.6 (d, J=5.1 Hz), 133.2, 132.8, 129.9, 129.5, 127.1 (d, J=1.9 Hz), 126.7, 122.2, 36.0 (d, J=21.5 Hz), 34.7 (d, J=64.2 Hz), 27.6 (d, J=5.0 Hz), 25.4, 10.8 (d, J=71.4 Hz), 5.0 (d, J=31.4 Hz). $^{31}$P NMR (202.5 MHz, CDCl$_3$) δ (ppm) 62.47 (d, J=4.0 Hz), 22.53 (d, J=4.0 Hz).

Example 13

Preparation of Catalyst 13A

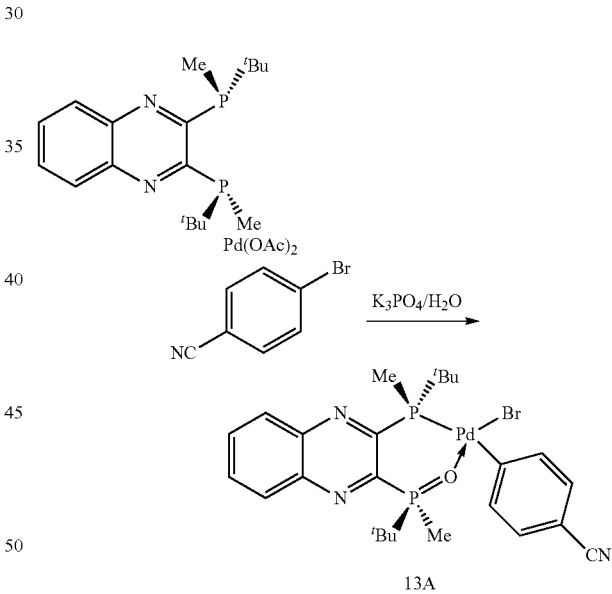

To a 1 L 3-neck flask with stirring bar was charged 4-bromobenzonitrile (3.40 g, 18.69 mmol), palladium(II) acetate (3.36 g, 14.95 mmol), (R) QuinoxP(R) (5 g, 14.95 mmol), then charged with degassed toluene (500 mL, KF ~5ppm) without stirring. Then the mixture was degassed by vacuum/refill with nitrogen 3 times, and swept with nitrogen above the surface for another 5 minutes. The mixture was then allowed to stir at room temperature for 1 hour to provide Solution A. To another 3-neck 1 L flask equipped with overhead stirrer was charged $K_3PO_4$ (31.7 g, 150 mmol) and toluene (100 mL). The reaction mixture was degassed by vacuum/refill nitrogen 3 times, then water was added (1.35 mL, 5 eq.). To the resulting solution was added Solution A via cannula, followed by water (5 eq.). $K_3PO_4$ (9 g) was then added to the reaction, and the resulting suspension was allowed to stir at room temperature for about 15 hours. The reaction mixture was then filtered, and the collected solids were washed with toluene. The filtrate was concentrated in vacuo to ~40 mL, then product seed was added. The resulting suspension was allowed to stir at room temperature for 4 hours, during which time a precipitate was formed. The reaction mixture was filtered, and the filter cake was washed with toluene and dried at room temperature under vacuum with nitrogen flow to provide 13A (7.40 g). The filtrate was concentrated in vacuo to ~100 mL, then product seed was added and the mixture was allowed to stir at room temperature for 3 hours. The mixture was then filtered and the filter cake was washed with toluene to provide a second crop of 13A (0.84 g). $^1$H NMR (500 MHz, CDCl$_3$): δ (ppm) 8.22-8.18 (2H, m), 8.02-8.00 (2H, m), 7.59 (1H, d, J=8.0 Hz), 7.36 (1H, d, J=8.0 Hz), 7.19 (1H, d, J=8.0 Hz), 7.14 (1H, d, J=8.0 Hz).1.99 (3H, d, J=13.0 Hz), 1.59 (9H, d, J=16.0 Hz), 1.26 (9H, d, J=16.0 Hz), 1.24 (3H, d, J=13.0 Hz); $^{31}$P NMR (202.5 MHz, CDCl$_3$) δ (ppm) 63.5 (d, J=4 Hz), 25.3 (d, J=4 Hz).

Example 14

Preparation of Catalyst 14C

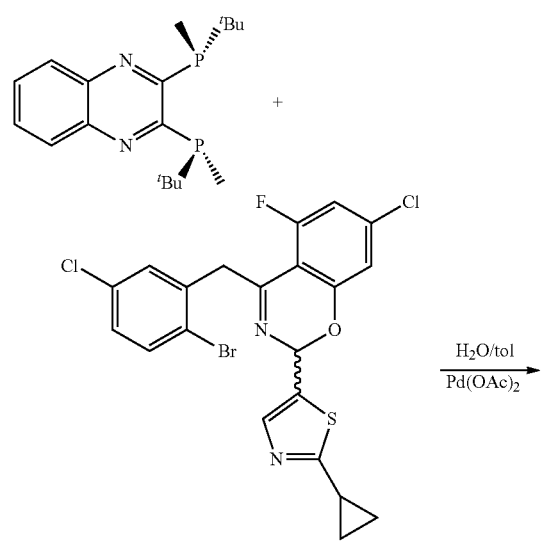

14A

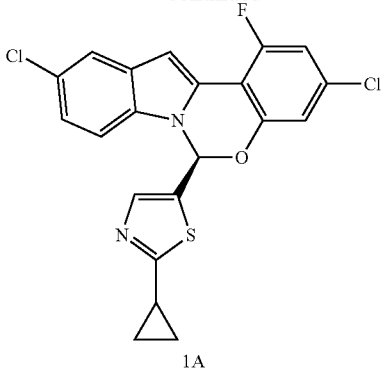

1A

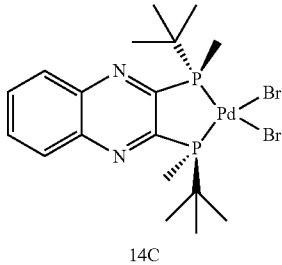

14C

A solution of diacetoxypalladium (113 mg, 0.502 mmol), (R) QuinoxP(R) (168 mg, 0.502 mmol), 14A (1.029 mg, 2.010 mmol) in toluene (35 mL) (~80 ppm) in a 40 mL vial was heated to 50° C. and allowed to stand at this temperature for about 15 hours. The reaction mixture was filtered and the collected solid was washed with toluene, then dried in vacuo under nitrogen flow at room temperature for about 88 hours to provide catalyst 14C as a solid (0.30 g). H NMR (500 MHz, CDCl$_3$): δ (ppm) 8.35-8.31 (m, 2H), 8.07-8.03 (m, 2H), 2.36 (6H, d, J=11. Hz), 1.22 (12H, d, J=16.5); $^{31}$P NMR (202.5 MHz, CDCl$_3$) δ (ppm) 54.90.

Example 15

Alternate Preparation of Intermediate Compound 1A

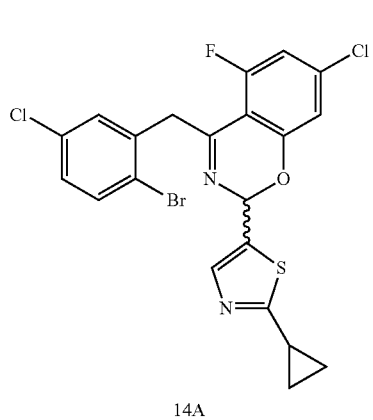

14A

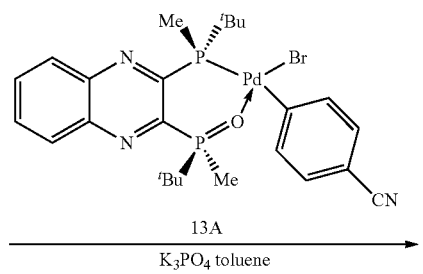

13A

K$_3$PO$_4$ toluene

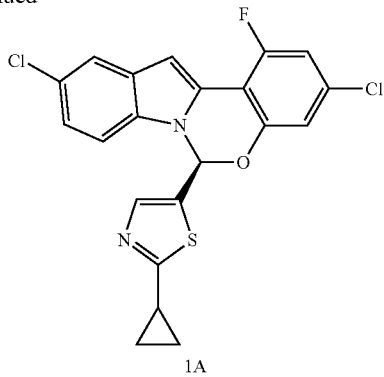

1A

To a 200 mL flask equipped with an overhead stirrer was charged pivalic acid (0.100 g, 0.976 mmol), 14A (5 g, 9.76 mmol), o-tolylboronic acid (0.093 g, 0.683 mmol), K$_3$PO$_4$ (5.18 g, 24.40 mmol), and toluene (125 mL), followed by 13A (0.062 g, 0.098 mmol). The resulting suspension was degassed under vacuum, then refilled with nitrogen for 3-4 times. The flask was swept with nitrogen above the surface for 5 minutes before being heated to 52° C., and the reaction was allowed to stir at this temperature for 20.5 hours to provide compound 1A (100% conversion).

Example 16

Alternate Preparation of Intermediate Compound 1A

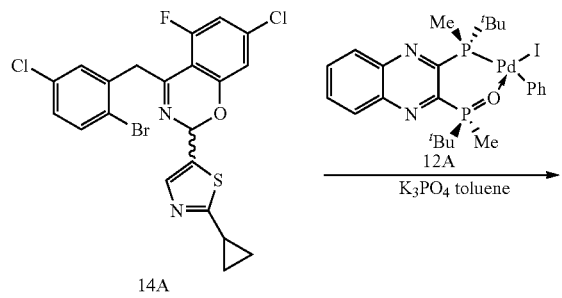

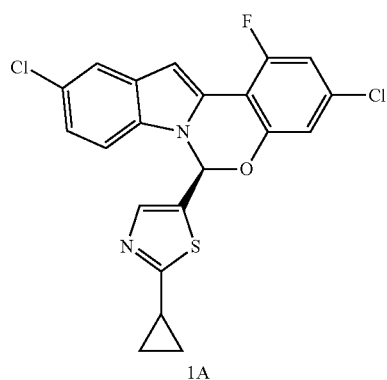

1A

In a glovebox, to a 30 mL vial equipped with stirring bar was charged pivalic acid (19.94 mg, 0.195 mmol, 0.1 eq.), 14A (1 g, 1.95 mmol), o-tolylboronic acid (18.58 mg, 0.137 mmol, 0.07 eq.), K$_3$PO$_4$ (1 g, 4.88 mmol, 2.5 eq.), and 12A (10.08 mg, 96% wt, 0.75% mmol). Then degassed toluene (25 mL) was added. The resulting mixture was capped and heated at 52° C. for 17 hours to provide compound 1A (100% conversion).

The following oxidative addition complex, 16A, was isolated along with compound B and is believed to be an active catalyst:

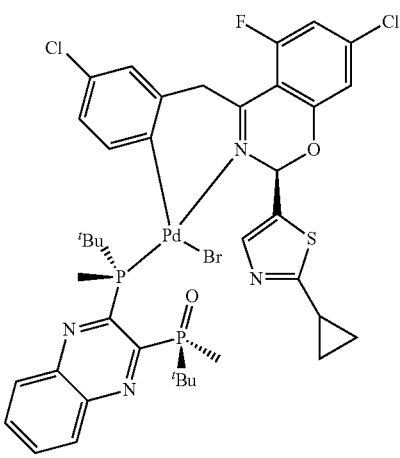

$^1$H NMR (500 MHz, toluene-d8) δ 0.43-0.56 (m, 2H, CH$_2$), 0.75-0.87 (m, 1H, CH$_2$), 0.91-0.98 (m, 1H, CH$_2$), 1.14 (d, J=14 Hz, 9H, CH$_3$), 1.57 (d, J=14 Hz, 9H, CH$_3$), 1.67-1.74 (m, 1H, CH), 1.95 (d, J=12 Hz, 3H, CH$_3$), 2.00 (d, J=12 Hz, 3H, CH$_3$), 4.05 (d, J=14 Hz, 1H, CH$_2$), 4.16 (d, J=14 Hz, 1H, CH$_2$), 6.05 (dd, J=11 and 2 Hz, 1H, CH), 6.4 (s, 1H, CH), 6.95-7.20 (m, 4H, CH), 7.6 (s, 1H, CH), 7.73 (d, J=8 Hz, 1H, CH), 7.77 (d, J=8 Hz, 1H, CH), 8.47 (s, 1H, CH), 8.55 (bs, 1H, CH) ppm; $^{31}$P NMR (202 MHz, toluene-d8) δ 48.6 (P=O) and 35.2 (P) ppm; LRMS-ESI m/z calcd. for C$_{39}$H$_{42}$Cl$_2$FN$_4$O$_2$P$_2$PdS$^+$: 887.09, found 887.24 [M-Br]$^+$.

Example 17

Alternate Preparation of Intermediate Compound 1A

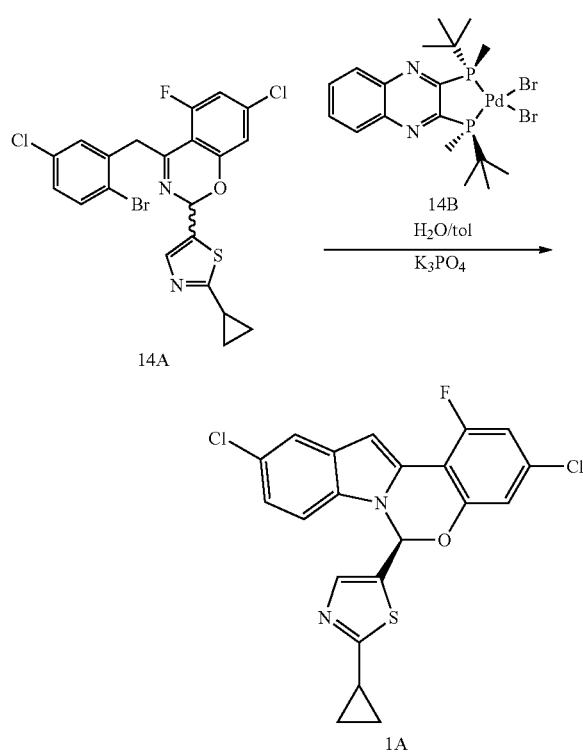

In glove box, to a suspension of 14B (2.93 mg, 2.5%) K₃PO₄ (228 mg, 1.074 mmol) in solution of 14A (100 mg) in degassed toluene (3000 µl) was charged water (5.28 mg, 0.293 mmol). The reaction mixture was allowed to stir at 55° C. for 18 hours to provide compound 1A (100% conversion, 90% ee).

Example 18

Alternate Preparation of Intermediate Compound 1A

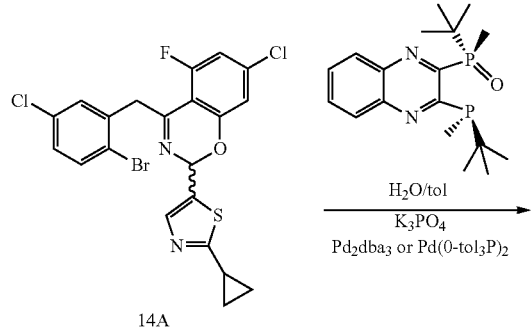

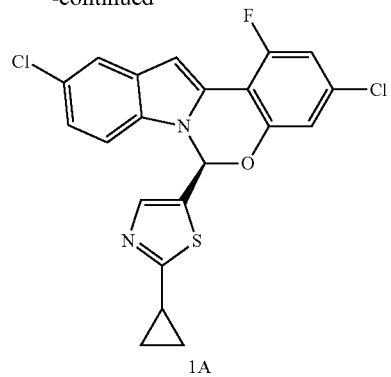

In a glove box, a solution of 14A (100 mg), POP ligand (1.58 mg, 0.022 eq.) and Pd(0) source (A: Pd₂dba₃, 1.79 mg, 0.01 eq. 1.95 umol; B: Pd(o-tol₃P)₂, 2.79 mg, 0.02 eq.) in degassed tol (3 mL) was heated at 50° C. for 1 hour, then charged with K₃PO₄ (0.145 g, 0.683 mmol) (3.5 eq.). The resulting mixture was allowed to stir at 50° C. to provide compound 1A. For A (Pd₂dba₃), after 19 hours, 100% conv.and 90% ee was achieved. For B (Pd(o-tol₃)₂), after 19 hours, 82% conversion and 90% ee was achieved.

Example 19

Crystal Structure Determination for Compound A

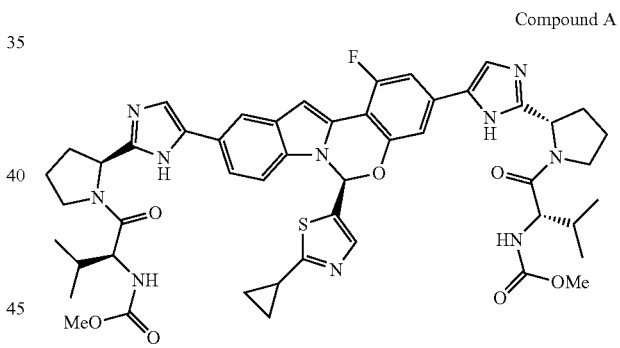

Compound A

Figure 3:
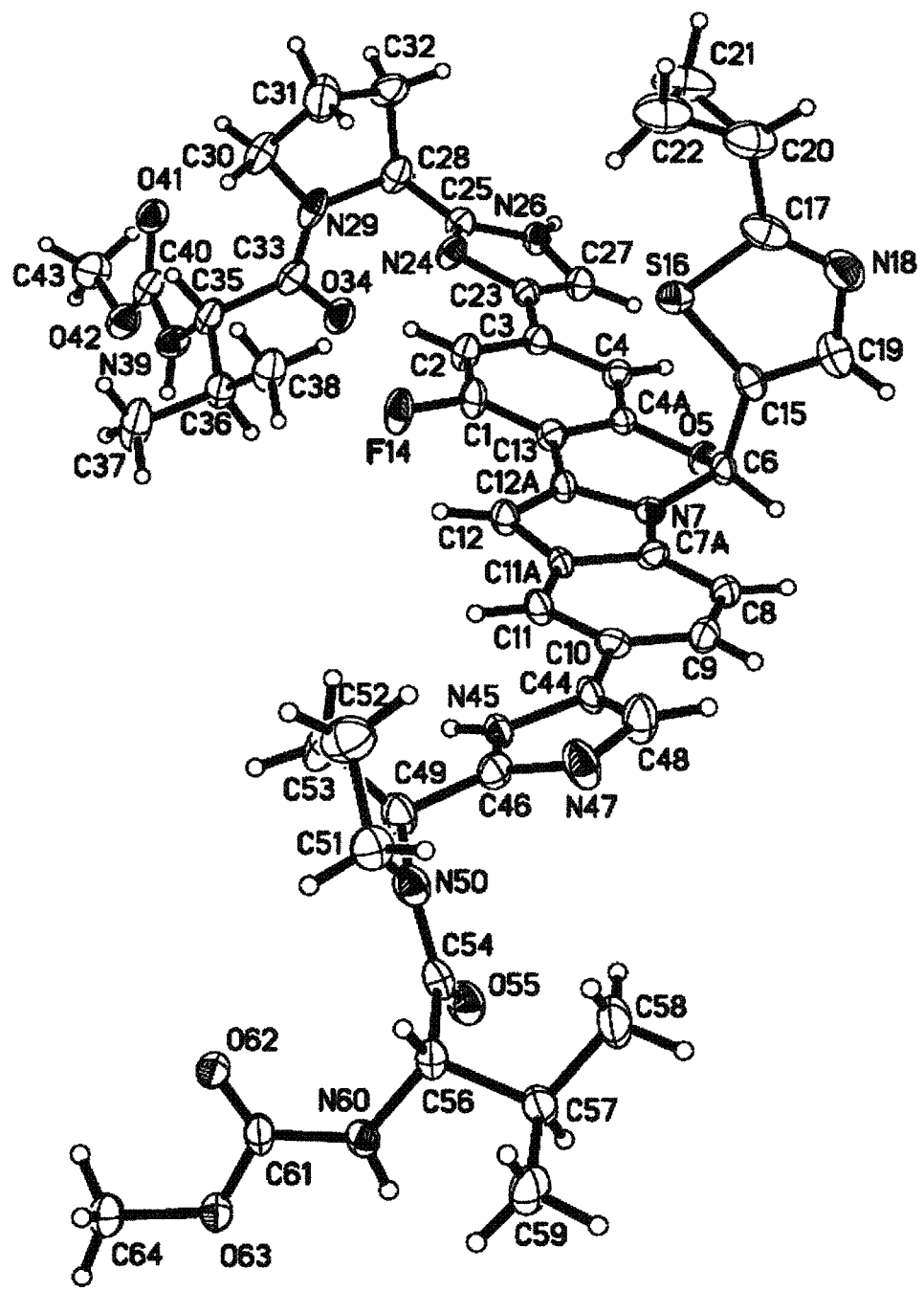
FIG. 3 shows a thermal ellipsoid representation of the x-ray crystal structure of compound A.

Single crystal structure determination was performed using a Bruker APEX 2 CCD diffractometer. Diffraction data were measured using monochromatized Cu Kα radiation. Full data acquisition for structure solution was performed at 100K. The crystal structure of Compound A was solved by single crystal X-ray analysis. The crystal form studied was determined to be a high order ethanol solvate in which the solvent was mainly disordered. The crystal structure confirmed the connectivity and the absolute stereochemistry of Compound A. Crystallographic information is shown below in Table 1. A thermal ellipsoid representation of Compound A is show in FIG. 3.

TABLE 1

| | |
|---|---|
| Formula, Formula weight (g/mol) | C₄₉ H₅₅ F N₁₀ O₇ S, 947.1* |
| Crystal system, Space group | Monoclinic, C2 |
| Cell lengths (Å) | a = 25.1816(18), b = 19.7356(13), c = 14.1869(10) |

TABLE 1-continued

| | |
|---|---|
| Cell angles (°) | α = 90.00, β = 99.581(4)., γ = 90.00 |
| V(Å³), Z, Z', D$_{calc}$ (g/ml) | 6952.2(8), 4, 1, 0.905* |
| μ(Cu Kα) (mm⁻¹) | 0.792* |
| F(000) | 2000* |
| Crystal size (mm) | 0.15 × 0.05 × 0.05 |
| Temperature (K) | 100 |
| Radiation (Å) | Cu Kα (1.54184) |
| Instrument | Bruker APEXII |
| Resolution (Å⁻³), max theta (°) | 0.84, 66.5 |
| Reflections: (Total, Unique, 2σ Obsd) | 46001, 12105, 11495 |
| Refined parameters | 619 |
| R, wR$_2$, S | 0.0566, 0.1625, 1.037 |
| Absolute Structure Parameter (Flack) | 0.105(10) |
| Max. residual density [e Å⁻³] | 0.531 |

*The formula and values utilizing the formula do not include the contribution from the disordered ethanol of crystallization While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:

1. A process for preparing a compound of Formula I:

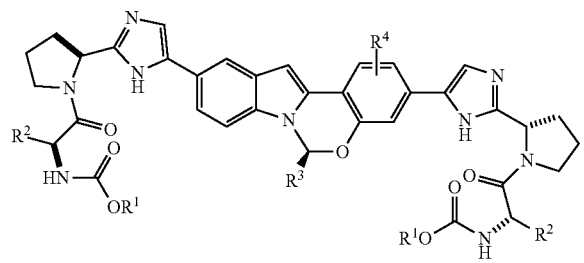

(I)

or a pharmaceutically acceptable salt thereof,
wherein said process comprises:
(A) contacting a compound of Formula II:

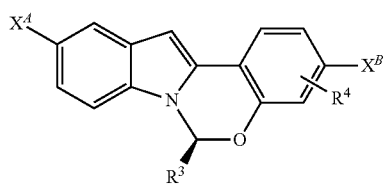

(II)

or a salt thereof, with bis(pinacoloato)diboron in the presence of a base, a transition metal catalyst, and an optional phosphorus ligand source, in an organic solvent A, for a time and at a temperature sufficient to provide an intermediate compound of Formula III:

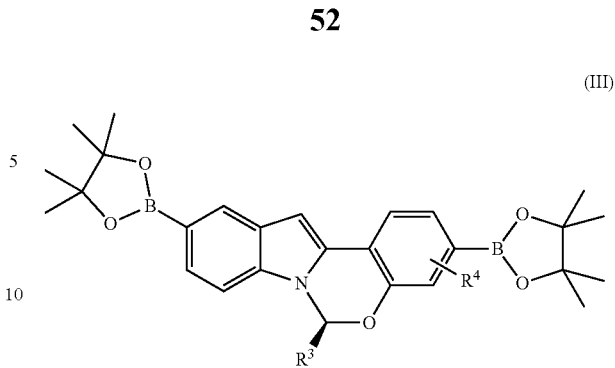

(III)

and (B) contacting the intermediate compound of formula III with a compound of formula IV:

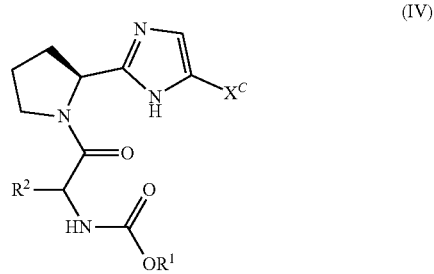

(IV)

in the presence of a base, a transition metal catalyst, an optional organic acid, and an optional phosphorus ligand source, in an organic solvent B, for a time and at a temperature sufficient to provide the compound of formula (I), wherein organic solvent A and organic solvent B are each independently selected from dimethylacetamide, toluene, acetonitrile, N,N-dimethylformamide, tetrahydrofuran, 2-methyl tetrahydrofuran, CPME, isopropanol, ethanol, ethyl acetate, water, isopropyl acetate and dimethoxyethane, and mixtures thereof,
and wherein:
$X^A$ is selected from Br, Cl, I and —OTf;
$X^B$ is selected from Br, Cl, I and —OTf;
$X^C$ is selected from Br, Cl, I and —OTf;
each occurrence of $R^1$ is independently selected from $C_1$-$C_6$ alkyl, $C_3$-$C_7$ cycloalkyl and $C_6$-$C_{10}$ aryl;
each occurrence of $R^2$ is independently selected from $C_1$-$C_6$ alkyl, $C_3$-$C_7$ cycloalkyl, 3 to 7-membered monocyclic heterocycloalkyl and $C_6$-$C_{10}$ aryl;
$R^3$ is selected from $C_1$-$C_6$ alkyl, $C_3$-$C_7$ cycloalkyl, $C_6$-$C_{10}$ aryl, 5 or 6-membered monocyclic heteroaryl and 9 or 10-membered bicyclic heteroaryl, wherein said $C_3$-$C_7$ cycloalkyl group, said $C_6$-$C_{10}$ aryl group, said 5 or 6-membered monocyclic heteroaryl group or said 9 or 10-membered bicyclic heteroaryl group can be optionally substituted with up to three groups, each independently selected from $C_1$-$C_6$ alkyl and $C_3$-$C_7$ cycloalkyl; and
$R^4$ represents up to 3 optional phenyl group substituents, which can be the same or different and are each independently selected from $C_1$-$C_6$ alkyl, —O—$C_1$-$C_6$ alkyl, halo, $C_1$-$C_6$ haloalkyl or —CN.

2. The process of claim 1, wherein:
Step A is conducted at a temperature in a range of from about 40° C. to about 110° C.;
the organic solvent A used in step A is selected from tetrahydrofuran, 2-methyl tetrahydrofuran, water, dimethoxyethane, isopropyl acetate, and mixtures thereof;

the base used in Step A is an acetate or pivalate base;
the transition metal catalyst used in Step A is selected from $Pd_2dba_3$, $Pd(OAc)_2$ and $PdCl_2$;
the optional phosphorus ligand used in Step A is present and is selected from $n\text{-}Bu(Ad)_2P$, Amphos, $n\text{-}BuP(t\text{-}Bu)_2\text{-}HBF_4$, XPhos, SPhos, BrettPhos, DTBPF, $PCy_3$ and $P(t\text{-}Bu)_3$;
Step B is conducted at a temperature in a range of from about 50° C. to about 120° C.;
the organic solvent B used in step B is selected from tetrahydrofuran, 2-methyl tetrahydrofuran, water, dimethoxyethane, isopropyl acetate, and mixtures thereof;
the base used in Step B is a carbonate or phosphate base;
the transition metal catalyst used in Step B is selected from $Pd_2dba_3$, $Pd(OAc)_2$ and $PdCl_2$; and
the optional phosphorus ligand used in Step B is present and is selected from $n\text{-}Bu(Ad)_2P$, Amphos, $n\text{-}BuP(t\text{-}Bu)_2\text{-}HBF_4$, XPhos, SPhos, BrettPhos, DTBPF, $PCy_3$ and $P(t\text{-}Bu)_3$.

3. The process of claim 2, wherein:
Step A is conducted at a temperature in a range of from about 50° C. to about 100° C.;
the organic solvent A used in step A is selected from tetrahydrofuran, 2-methyl tetrahydrofuran, dimethoxyethane, water, and mixtures thereof;
the base used in Step A is an alkali metal acetate base;
the transition metal catalyst used in Step A is $Pd(OAc)_2$;
the optional phosphorus ligand used in Step A is present and is selected from XPhos, SPhos and BrettPhos;
Step B is conducted at a temperature in a range of from about 65° C. to about 90° C.;
the organic solvent B used in step B is selected from tetrahydrofuran, 2-methyl tetrahydrofuran, water, and mixtures thereof;
the base used in Step B is an alkali metal carbonate base;
the transition metal catalyst used in Step B is $Pd(OAc)_2$; and
the optional phosphorus ligand used in Step B is present and is selected from XPhos, SPhos and BrettPhos.

4. The process of claim 3, wherein:
Step A is conducted at a temperature in a range of from about 50° C. to about 100° C.;
the organic solvent A used in step A is a mixture of 2-methyl tetrahydrofuran and water;
the acetate or pivalate base used in Step A is KOAc;
the transition metal catalyst used in Step A is $Pd(OAc)_2$;
the optional phosphorus ligand used in Step A is present and is selected from XPhos;
Step B is conducted at a temperature in a range of from about 50° C. to about 90° C.;
the organic solvent B used in step B is a mixture of 2-methyl tetrahydrofuran and water;
the carbonate acetate or pivalate base used in Step B is potassium carbonate;
the transition metal catalyst used in Step B is $Pd(OAc)_2$; and
the optional phosphorus ligand used in Step B, is present and is XPhos.

5. The process of claim 1, wherein each occurrence of $R^1$ and $R^2$ is independently $C_1\text{-}C_6$ alkyl and $R^3$ is 5 or 6-membered heteroaryl or $C_6\text{-}C_{10}$ aryl, wherein $R^3$ can be optionally substituted with a group selected from $C_1\text{-}C_6$ alkyl and $C_3\text{-}C_7$ cycloalkyl.

6. The process of claim 1, wherein the compound of formula (I) has the structure:

wherein said process comprises the steps:
(A) contacting a compound of Formula IIa:

(IIa)

with bis(pinacoloato)diboron in the presence of an acetate or pivalate base, a palladium catalyst, and a phosphorus ligand source, in a mixture of water and an organic solvent A, for a time and at a temperature sufficient to provide an intermediate compound of Formula IIIa:

(IIIa)

;

and
(B) contacting the intermediate compound of formula IIIa with a compound of formula IVa:

(IVa)

in the presence of a carbonate base or a phosphate base, a palladium catalyst, and a phosphorus ligand source, in a mixture of water and organic solvent B, for a time and at a temperature sufficient to provide compound A, wherein organic solvents A and B are each independently selected from tetrahydrofuran, 2-methyl tetrahydrofuran, dimethoxyethane, toluene, ethyl acetate and isopropyl acetate; $X^A$ is selected from Br, Cl and I; $X^B$ is selected from Br, Cl and I; and $X^C$ is selected from Br, Cl and I.

7. A process for preparing a compound of Formula I:

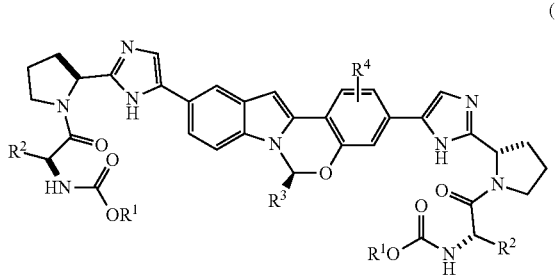

(I)

or a pharmaceutically acceptable salt thereof,
wherein said process comprises contacting an intermediate compound of formula III:

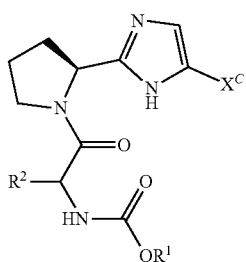

(III)

with a compound of formula IV:

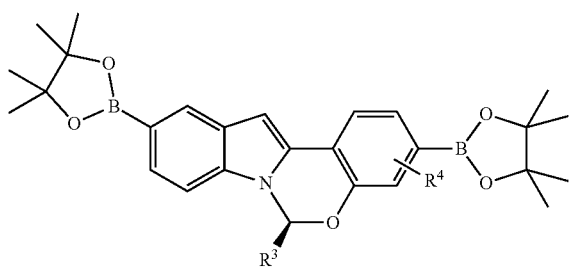

(IV)

in the presence of a carbonate base or phosphate base and a transition metal catalyst, and optionally in the presence of a phosphorus ligand source, in a mixture of water and organic solvent B, for a time and at a temperature sufficient to provide the compound of formula (I), wherein organic solvent B is selected from dimethylacetamide, toluene, acetonitrile, N,N-dimethylformamide, tetrahydrofuran, 2-methyl tetrahydrofuran, CPME, isopropanol, ethanol, ethyl acetate, water, isopropyl acetate and dimethoxyethane, and mixtures thereof,
and wherein:
$X^C$ is selected from Br, Cl, I and —OTf;
each occurrence of $R^1$ is independently selected from $C_1$-$C_6$ alkyl, $C_3$-$C_7$ cycloalkyl and $C_6$-$C_{10}$ aryl;
each occurrence of $R^2$ is independently selected from $C_1$-$C_6$ alkyl, $C_3$-$C_7$ cycloalkyl, 3 to 7-membered monocyclic heterocycloalkyl and $C_6$-$C_{10}$ aryl;

$R^3$ is selected from $C_1$-$C_6$ alkyl, $C_3$-$C_7$ cycloalkyl, $C_6$-$C_{10}$ aryl, 5 or 6-membered monocyclic heteroaryl and 9 or 10-membered bicyclic heteroaryl, wherein said $C_3$-$C_7$ cycloalkyl group, said $C_6$-$C_{10}$ aryl group, said 5 or 6-membered monocyclic heteroaryl group or said 9 or 10-membered bicyclic heteroaryl group can be optionally substituted with up to three groups, each independently selected from $C_1$-$C_6$ alkyl and $C_3$-$C_7$ cycloalkyl; and $R^4$ represents up to 3 optional phenyl group substituents, which can be the same or different and are each independently selected from $C_1$-$C_6$ alkyl, —O—$C_1$-$C_6$ alkyl, halo, $C_1$-$C_6$ haloalkyl or —CN.

8. The process of claim 7, wherein:
said process is conducted at a temperature in a range of from about 50° C. to about 90° C.;
the organic solvent B used is selected from tetrahydrofuran, 2-methyl tetrahydrofuran, dimethoxyethane, water, and mixtures thereof;
the base used is an alkali metal carbonate base;
the transition metal catalyst used is $Pd(OAc)_2$; and
the optional phosphorus ligand is present and is selected from XPhos, SPhos and BrettPhos.

9. The process of claim 1, wherein each occurrence of $R^1$ is methyl and each occurrence of $R^2$ is isopropyl.

10. The process of claim 1, wherein $R^3$ is phenyl, thiazolyl or thiophenyl, each of which can be optionally substituted with a $C_3$-$C_7$ cycloalkyl group.

11. The process of claim 1, wherein the compound of formula (IV) is:

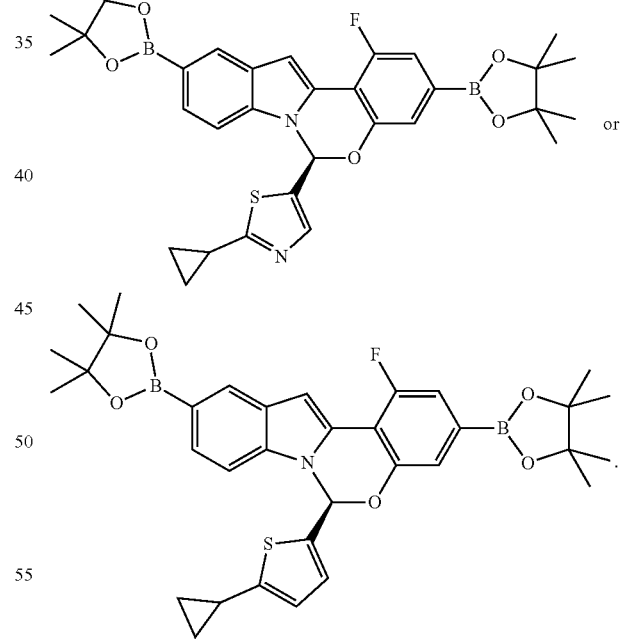

12. The bis-mandelate salt of the compound of claim 11.
13. The ethnoal solvate of the compound of claim 11.
14. The process of claim 7, wherein each occurrence of $R^1$ is methyl; and each occurrence of $R^2$ is isopropyl.
15. The process of claim 7, wherein $R^3$ is phenyl, thiazolyl or thiophenyl, each of which can be optionally substituted with a $C_3$-$C_7$ cycloalkyl group.

* * * * *